(12) United States Patent
Kaji et al.

(10) Patent No.: US 8,460,314 B2
(45) Date of Patent: Jun. 11, 2013

(54) APPLICATION OF PROCEDURE THROUGH NATURAL ORIFICE

(75) Inventors: Kunihide Kaji, Hachioji (JP); Masatoshi Sato, Yokohama (JP)

(73) Assignee: Olympus Medical Systems Corp., Tokyo (JP)

( * ) Notice: Subject to any disclaimer, the term of this patent is extended or adjusted under 35 U.S.C. 154(b) by 651 days.

(21) Appl. No.: 11/710,733

(22) Filed: Feb. 26, 2007

(65) Prior Publication Data
US 2008/0208161 A1    Aug. 28, 2008

(51) Int. Cl.
*A61B 17/22* (2006.01)
(52) U.S. Cl.
USPC .......................................................... 606/128
(58) Field of Classification Search
USPC ...................... 600/101–183; 604/19, 48, 500; 606/110–115, 127–128
See application file for complete search history.

(56) References Cited

U.S. PATENT DOCUMENTS

| | | | | | |
|---|---|---|---|---|---|
| 4,414,962 | A | * | 11/1983 | Carson | 600/138 |
| 5,037,433 | A | * | 8/1991 | Wilk et al. | 606/139 |
| 5,330,503 | A | * | 7/1994 | Yoon | 606/223 |
| 5,459,177 | A | * | 10/1995 | Miyakoshi et al. | 523/111 |
| 6,093,196 | A | * | 7/2000 | Okada | 606/127 |
| 2002/0111534 | A1 | * | 8/2002 | Suzuki et al. | 600/102 |
| 2003/0069533 | A1 | * | 4/2003 | Kakutani et al. | 604/8 |
| 2003/0092689 | A1 | * | 5/2003 | Escandon et al. | 514/171 |
| 2005/0055053 | A1 | * | 3/2005 | Phalen et al. | 607/1 |
| 2008/0255476 | A1 | * | 10/2008 | Boyajian et al. | 600/593 |

* cited by examiner

*Primary Examiner* — Ryan Severson
*Assistant Examiner* — Ashley Cronin
(74) *Attorney, Agent, or Firm* — Scully, Scott, Murphy & Presser, P.C.

(57) ABSTRACT

The application of the procedure through a natural orifice of the present invention includes the steps of: inserting a flexible endoscope through the natural orifice to the alimentary tract; incising the close-contact portion of the alimentary tract and the gall bladder under a guidance of a device for identifying the positional relationship from the alimentary tract side and forming an puncture; extracting stones in the gall bladder from the body; and removing the endoscope after completing the procedure.

34 Claims, 40 Drawing Sheets

APPLICATION OF PROCEDURE THROUGH NATURAL ORIFICE

BACKGROUND OF THE INVENTION

1. Field of the Invention

The present invention relates to the method of treating cholecystolithiasis by procedure through a natural orifice.

2. Description of Related Art

Laparoscopic operations are a well-known procedure for body organs performed upon inserting medical instruments transcutaneously. That is, small incisions are made at multiple locations on the abdomen, a trocar is inserted, and a gas such as carbon dioxide is injected in the abdominal cavity to create pneumoperitoneum. Moreover, a laparoscope or a forceps is inserted through the trocar and the procedures are performed while confirming the images of the inside of the abdominal cavity taken by the laparoscope.

Laparoscopic cholecystectomy is one of the examples of transcutaneous procedure performed in this procedure. This surgery is generally performed as part of the treatment of cholelithiasis. The definitive cholecystectomy; the extraction of the gall bladder together with gallstone is generally performed because even if only stones are extracted, there is a high probability that a stone will be formed again in the gall bladder. Specifically, using a medical instrument inserted in the abdominal cavity through the trocar, the gall bladder duct and the cystic artery connected to the gall bladder is detached from the surrounding and ligated; thereafter, they are dissected and the gall bladder body is isolated. After isolating the gall bladder from the liver, the gall bladder is removed from the body through the small incision made in the abdomen.

SUMMARY OF THE INVENTION

The present invention has the main object of offering a superior and less invasive method, even from cosmetic aspects, for performing procedures (treatment) through a natural orifice equivalent to the cholecystectomy that has conventionally been performed as a laparoscopic procedure.

The procedure through a natural orifice related to the first aspect of the present invention includes the steps of: inserting a flexible endoscope through a natural orifice to the alimentary tract; incising a close-contact portion of the alimentary tract and the gall bladder under a guidance of a device for identifying positional relationship from the alimentary tract side and forming a puncture; extracting stones in the gall bladder from the body; and removing the endoscope after completing the procedure.

The procedure through a natural orifice related to the second aspect of the present invention includes the steps of: inserting a flexible endoscope through a natural orifice to the alimentary tract; joining the alimentary tract and the gall bladder in close contact each other; forming a puncture in the close contact portion; extracting stones in the gall bladder from the body; and removing the endoscope after completing the procedure.

The procedure through a natural orifice related to the third aspect of the present invention includes the steps of: inserting a flexible endoscope through a natural orifice to the alimentary tract; joining the alimentary tract and the gall bladder close contact each other; and fixing them so that a fistulous opening can be formed; removing the endoscope; and inserting the endoscope again through natural orifice and performing the procedure after forming the fistulous opening.

DETAILED DESCRIPTION OF THE INVENTION

Embodiments are described here. The same reference numbers are affixed to the same elements in each mode of the embodiments. Duplication of explanations is omitted. In each of the embodiments below, the procedure to make bypass between the duodenum, which is the upper alimentary tract, and the gall bladder is described, but a different upper alimentary tract, such as the stomach and the gall bladder may also be linked.

First Embodiment

Figure 1:
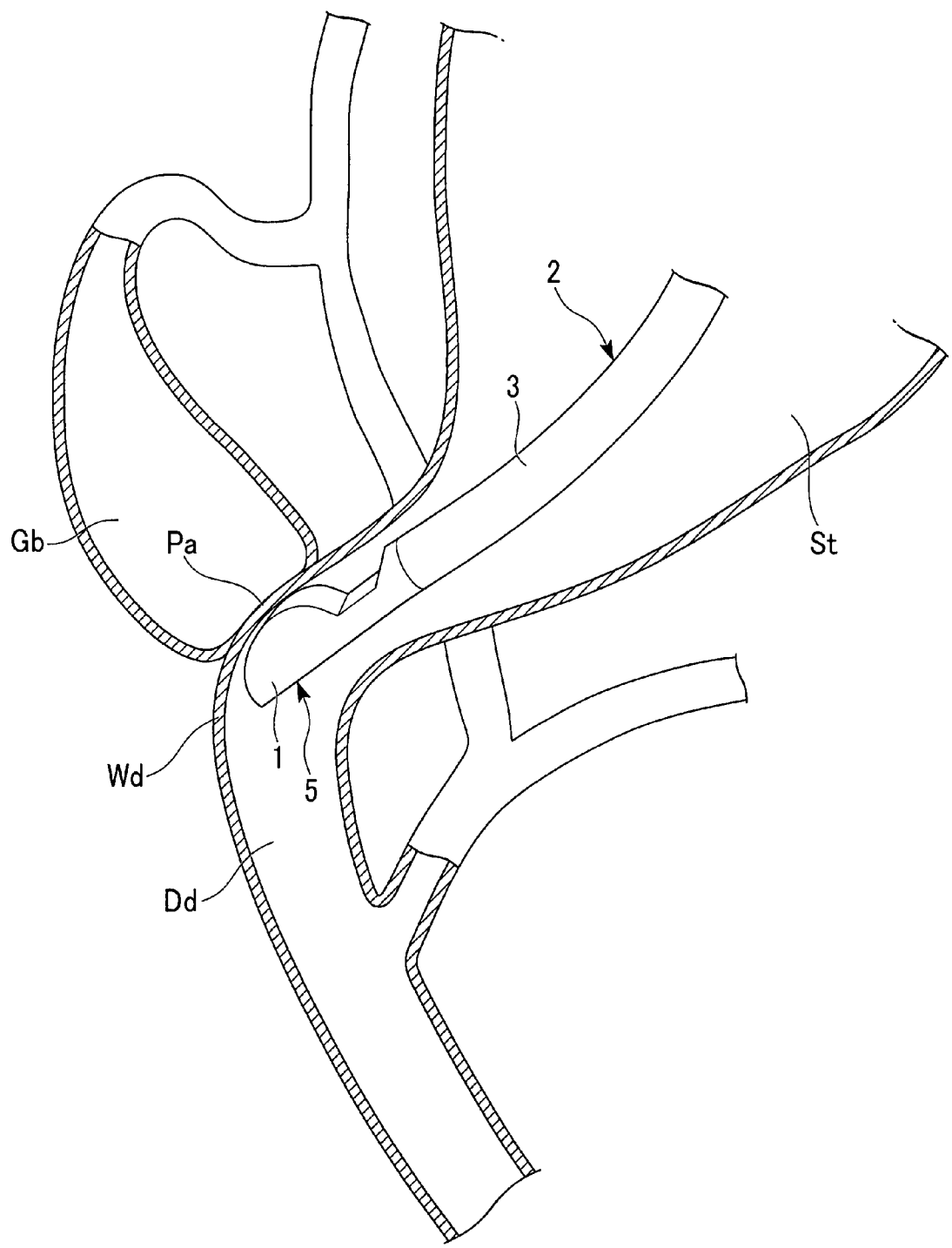
FIG. 1 shows the procedure to confirm the coalesced portion by an ultrasonic endoscope.
Figure 2:
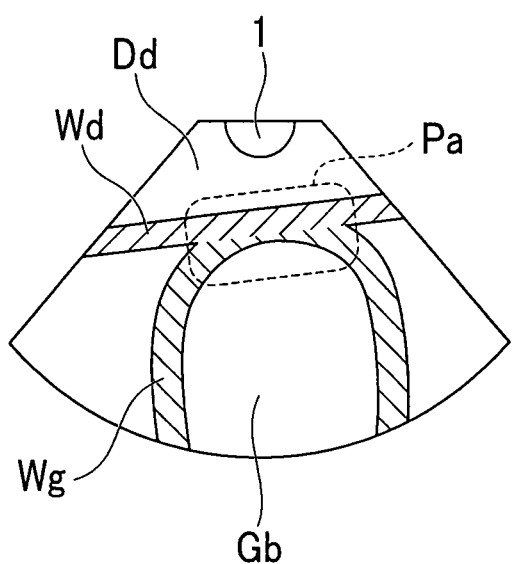
FIG. 2 shows the schematic diagram of the ultrasonic image of the coalesced portion.

As shown in FIG. 1, this embodiment relates to the case wherein the gall bladder Gb is coalesced with the duodenum Dd which is the upper alimentary tract organ, and the procedure is performed through a natural orifice. According to the present embodiment, an ultrasonic probe 1 inserted in the body is used as the device for understanding the positional relationship to confirm the positions of the gall bladder Gb and the duodenum Dd. The ultrasonic probe 1 is fitted to the front end of the insertion portion 3 having the flexibility of the endoscope 2, and bulges out on the flat surface and over the axial line of the insertion portion 3. A plurality of ultrasonic transducers is disposed along the periphery of circular arc shape. The endoscope 2 provided with the ultrasonic probe 1 is inserted through the patient's mouth. If an ultrasonic image is obtained, the coalesced portion Pa of the gall bladder wall Wg and the duodenum wall Wd can be confirmed, as shown in FIG. 2.

Other ultrasonic probes used outside the body, Computerized Tomography (CT), Magnetic Resonance Imaging (MRI), X-ray photography and so on can also be used as devices for understanding positional relationships.

Figure 3:
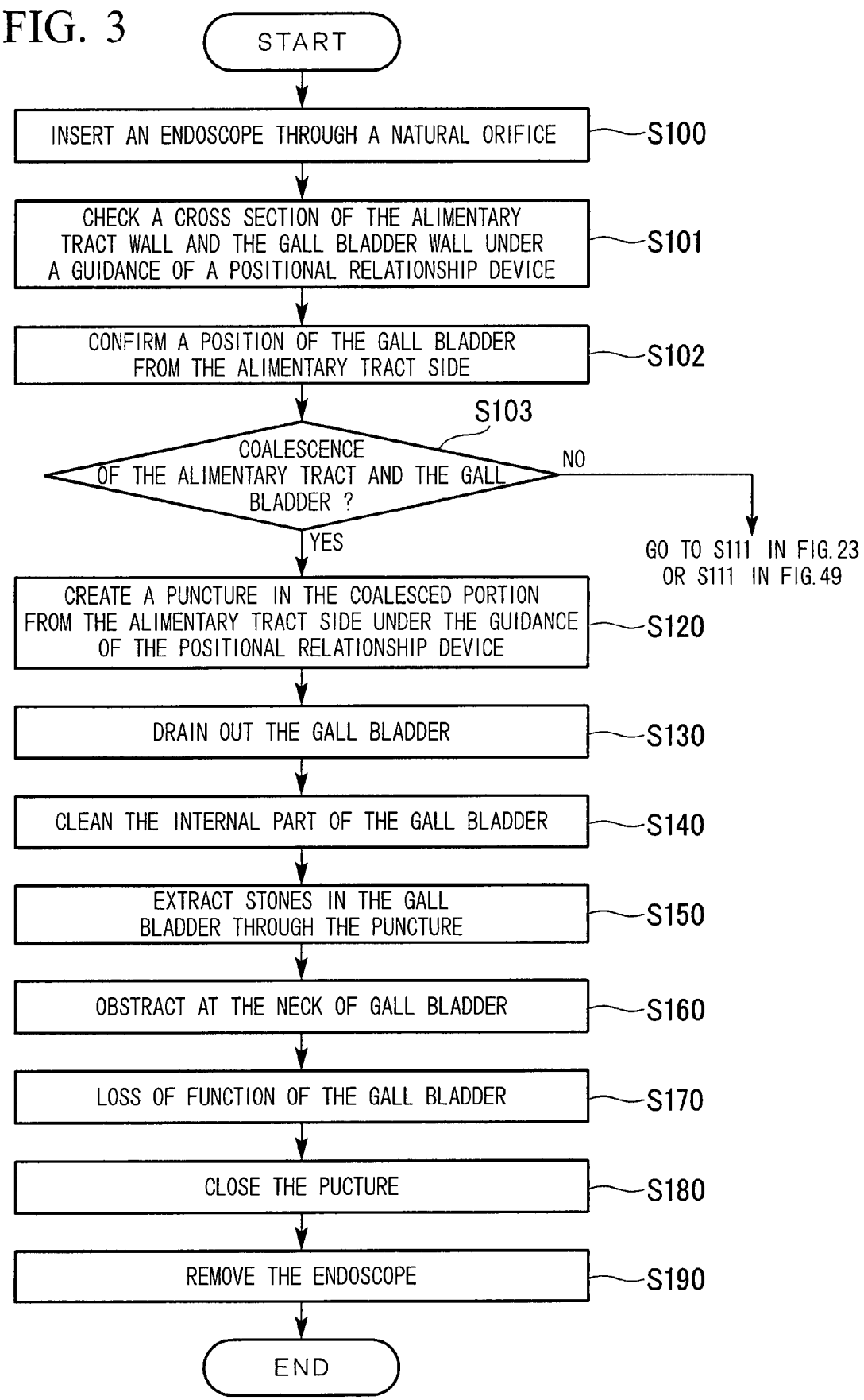
FIG. 3 is a flow chart describing the procedure of the first embodiment.

FIG. 3 shows a flow chart for procedure in the present embodiment. First, the endoscope 2 is inserted through a natural orifice (step S100), and the position of the gall bladder Gb is confirmed from the alimentary tract side (step S101). Next, the cross section of the alimentary tract wall and the gall bladder wall Wg are checked under a guidance of a positional relationship device (step 102). After checking the coalescence of the alimentary tract and the gall bladder Gb; if the two have not coalesced ("No" in step S103), step S111 of FIG. 23 or step S111 of FIG. 49 of a procedure related to another embodiment mentioned later, are implemented.

Figure 4:
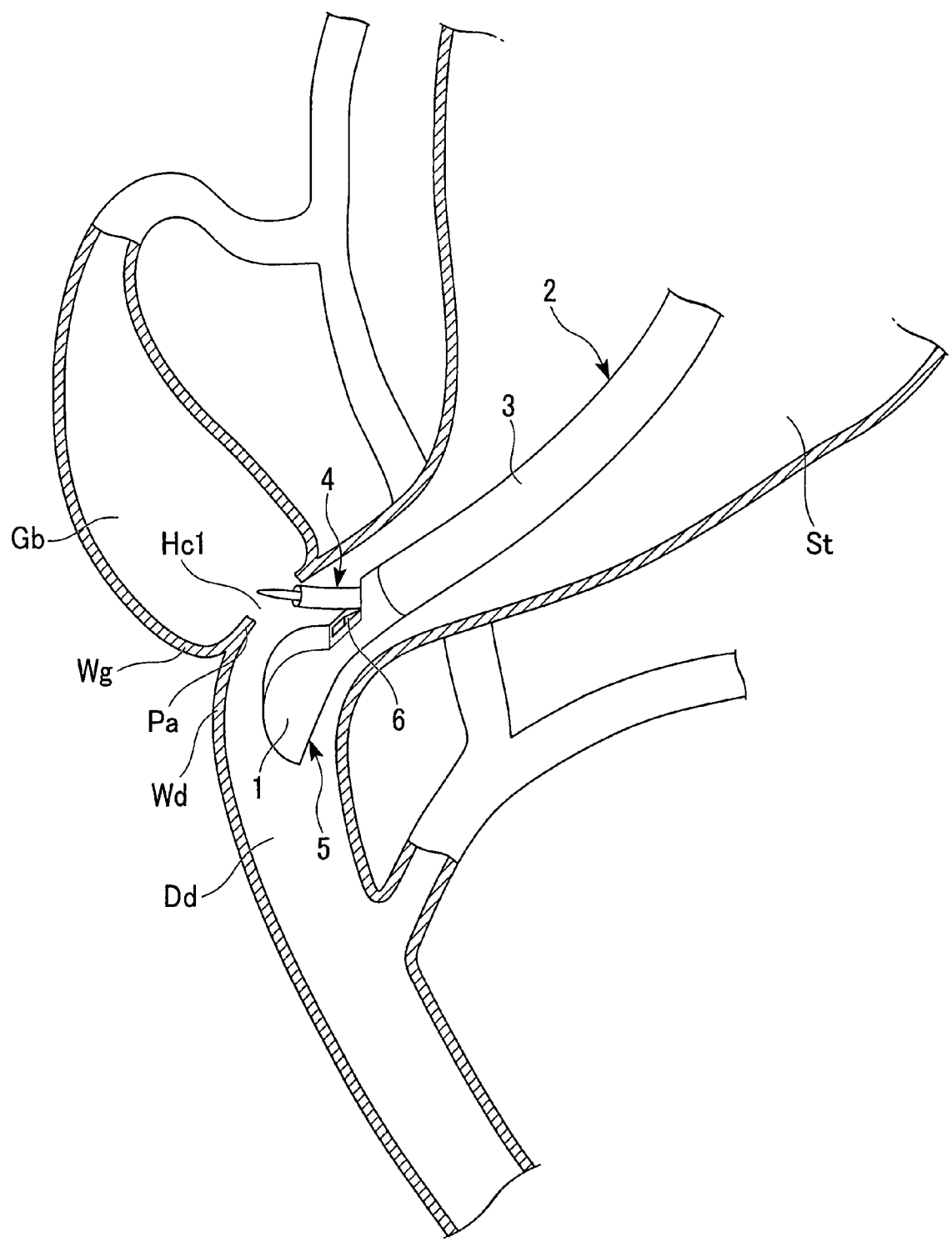
FIG. 4 shows the formation of puncture in the coalesced portion.

In contrast, if there is coalescence ("Yes" in step S103), a puncture is created in the coalesced portion Pa (step S120) from the alimentary tract side under the guidance of the positional relationship device. The gall bladder Gb is drained out (step S130) and subsequently, the internal part of the gall bladder Gb is cleaned (step S140). Stones in the gall bladder Gb are extracted through the puncture (step S150) and the neck of gall bladder is obstructed (step S160). After the loss of function of the gall bladder Gb (step S170), the puncture is closed (step S180), and the endoscope 2 is removed (step 190). During the procedure of step S120, as shown in FIG. 4, under a guidance of the ultrasonic probe 1, the coalesced portion Pa formed between the duodenum wall Wd and the gall bladder wall Wg, is incised by the incising device 4 through the endoscope 2 from the duodenum Dd side, and the puncture Hc1 is created. A needle knife or a high-frequency knife may be used as the incising device 4. Such a device 4 is passed through the instrument channel of the endoscope 2, and delivered to the coalesced portion Pa from the forceps elevator 6 installed on the front end cover 5. Since an image pickup apparatus (not shown in the figures) is provided in the front end cover 5, the desired locations can be incised while monitoring the images of internal parts of the body obtained by the image pickup apparatus.

The drainage in step S130 is the natural expulsion of bile accumulated in the gall bladder Gb to the duodenum Dd through the puncture Hc1.

Figure 5:
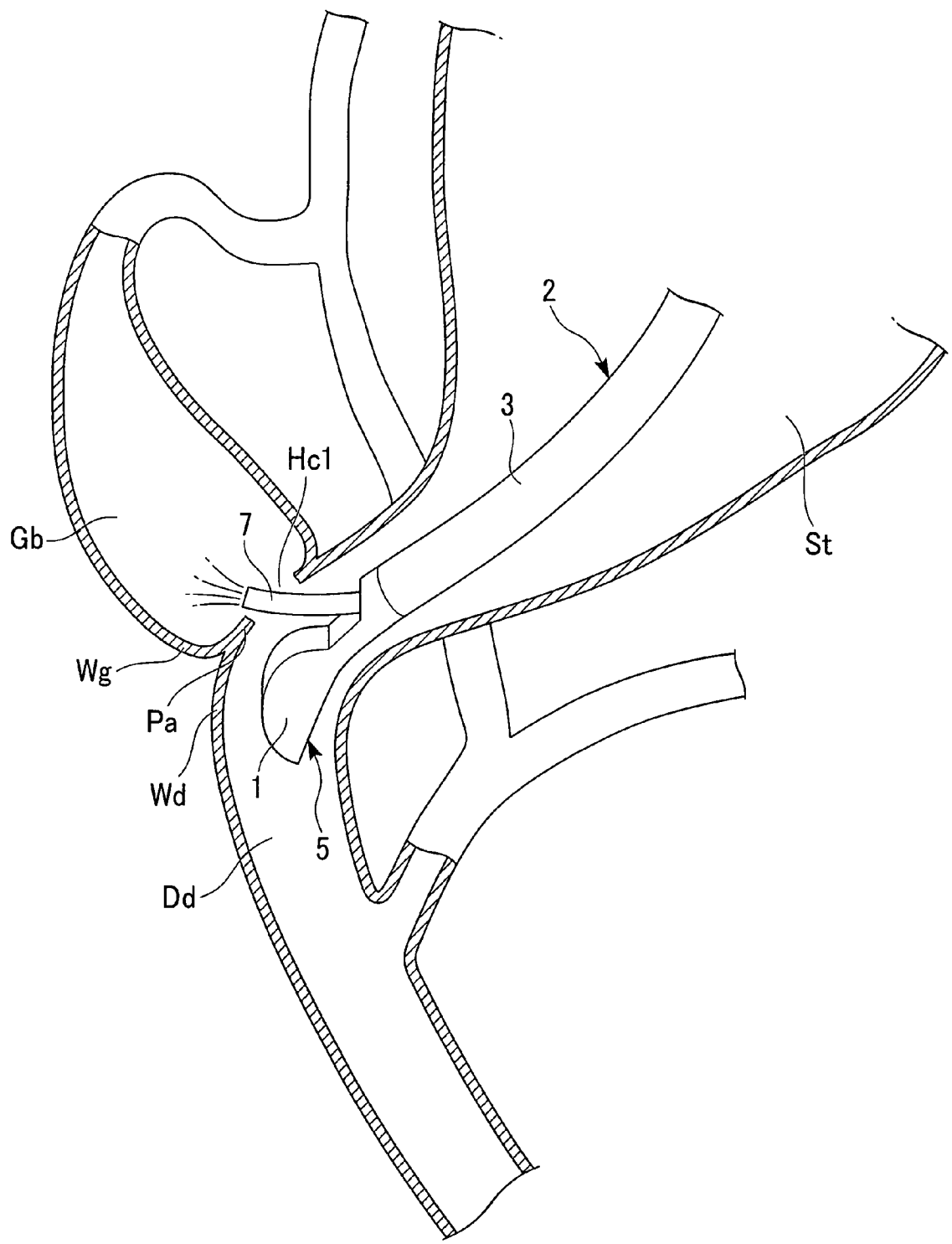
FIG. 5 shows the cleaning the gall bladder by the liquid delivery tube.

As shown in FIG. 5, during the cleaning in step S140, the cleaning tube 7 through the instrument channel of the endoscope 2 is delivered into the gall bladder Gb from the puncture Hc1. The gall bladder Gb is cleaned by injecting fluid such as saline solution from the cleaning tube 7. If the size of the puncture Hc1 is made smaller than the diameter of the cleaning tube 7, watertightness of the puncture Hc1 and the cleaning tube 7 can be ensured, the saline solution does not leak into the duodenum Dd side, and efficient cleaning can be achieved.

Figure 6:
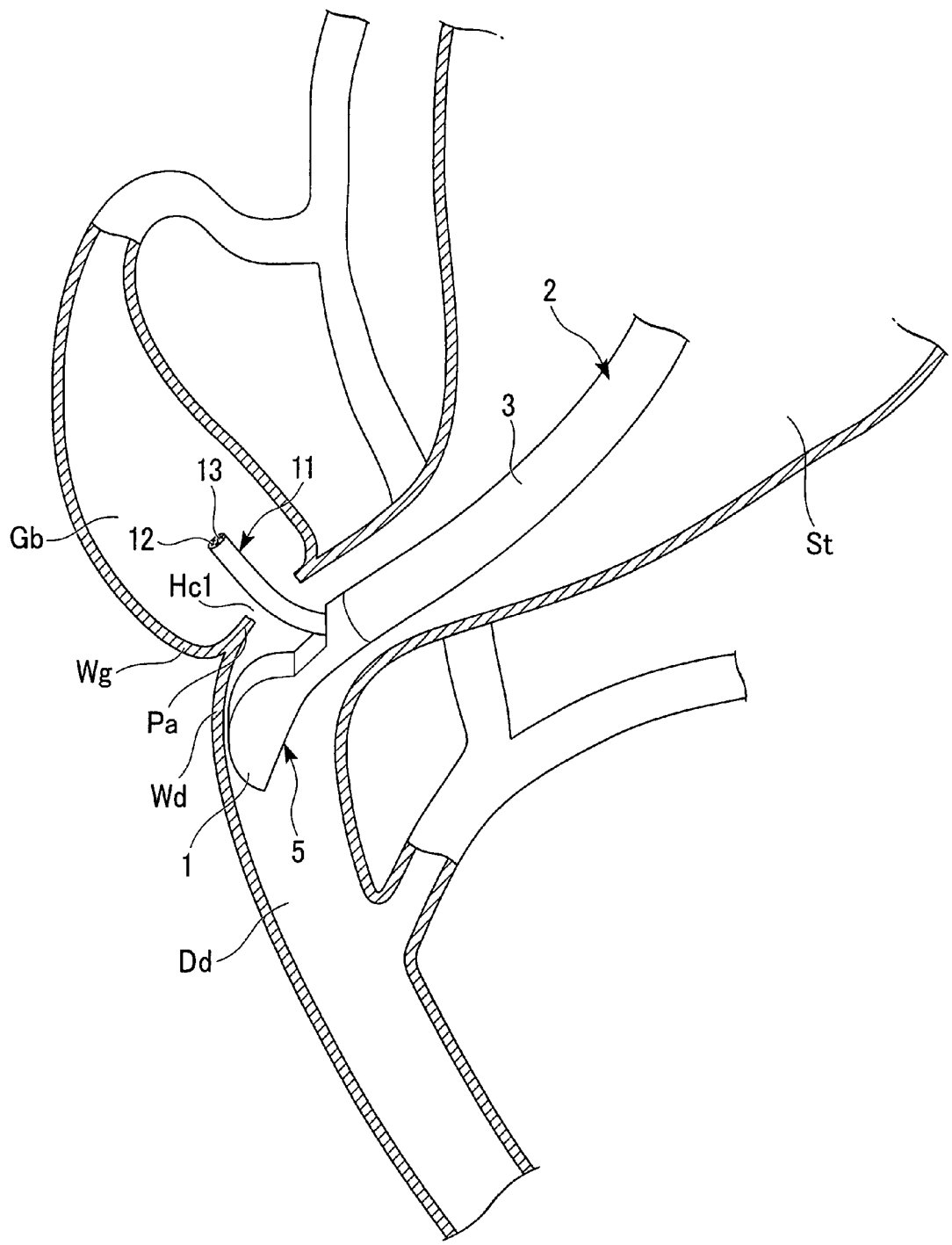
FIG. 6 shows a small endoscope inserted in the gall bladder.

The procedure from step S150 to step S170 is performed within the gall bladder Gb. In the present embodiment, a small device having an image pickup apparatus is inserted from the puncture Hc1 to perform the treatment within the gall bladder Gb. As shown in FIG. 6, the small device, endoscope 11 is provided with an image pickup apparatus 12, and an opening for the instrument channel 13 at the front end. When the small endoscope 11 is used, a small puncture Hc1 is adequate.

Figure 7:
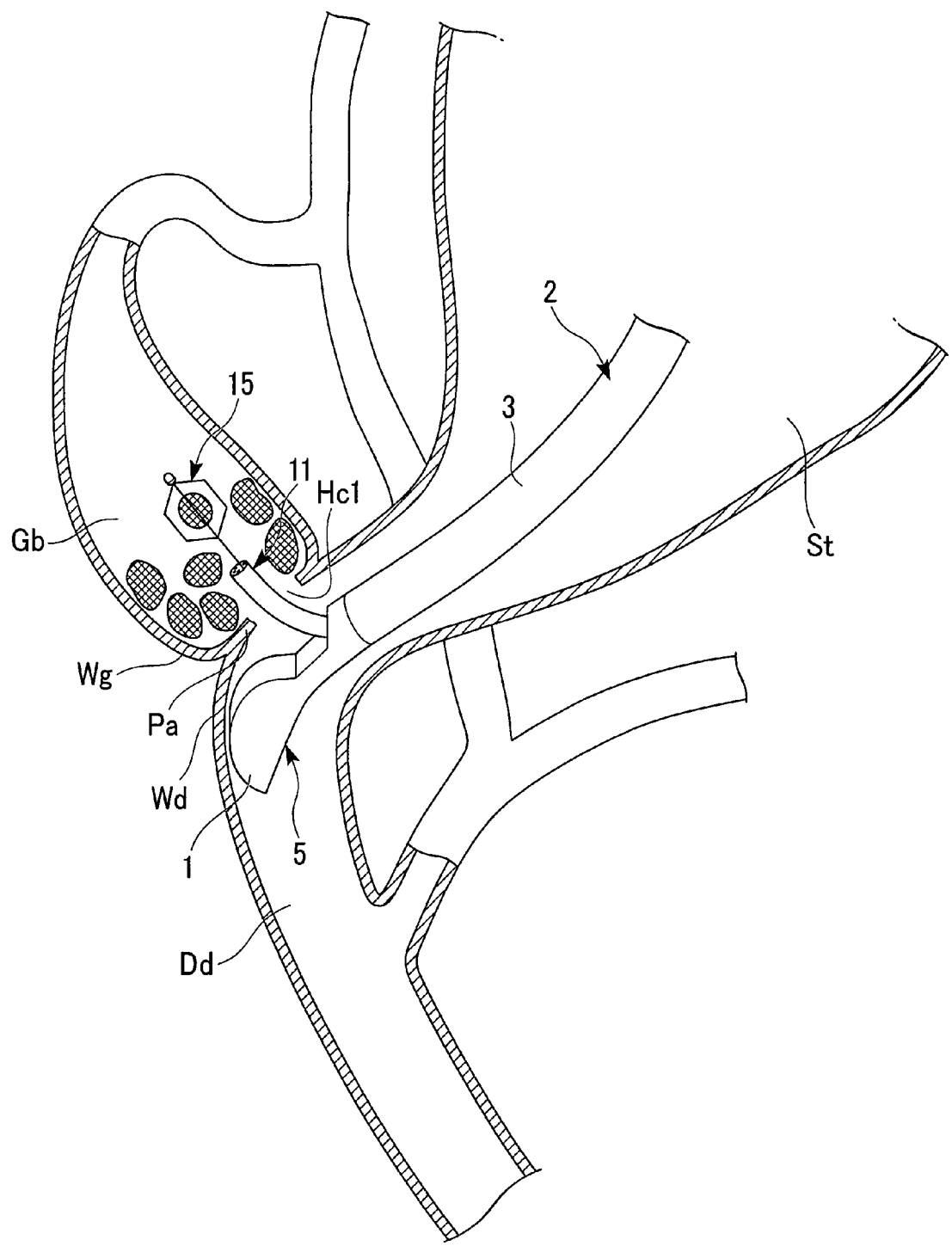
FIG. 7 shows the extraction of stones by a stone removal tool.

Next, stones in the gall bladder Gb are extracted through the puncture Hc1. As shown in FIG. 7, the stone removal tool 15 is inserted into the gall bladder Gb from the instrument channel 13 of the small endoscope 11 and stones are extracted. The image within the gall bladder Gb is monitored using the image pickup apparatus 12. If the stone is large, a stone crushing tool such as extracorporal shock wave lithotripsy probe or Dormia basket is used.

Figure 8:
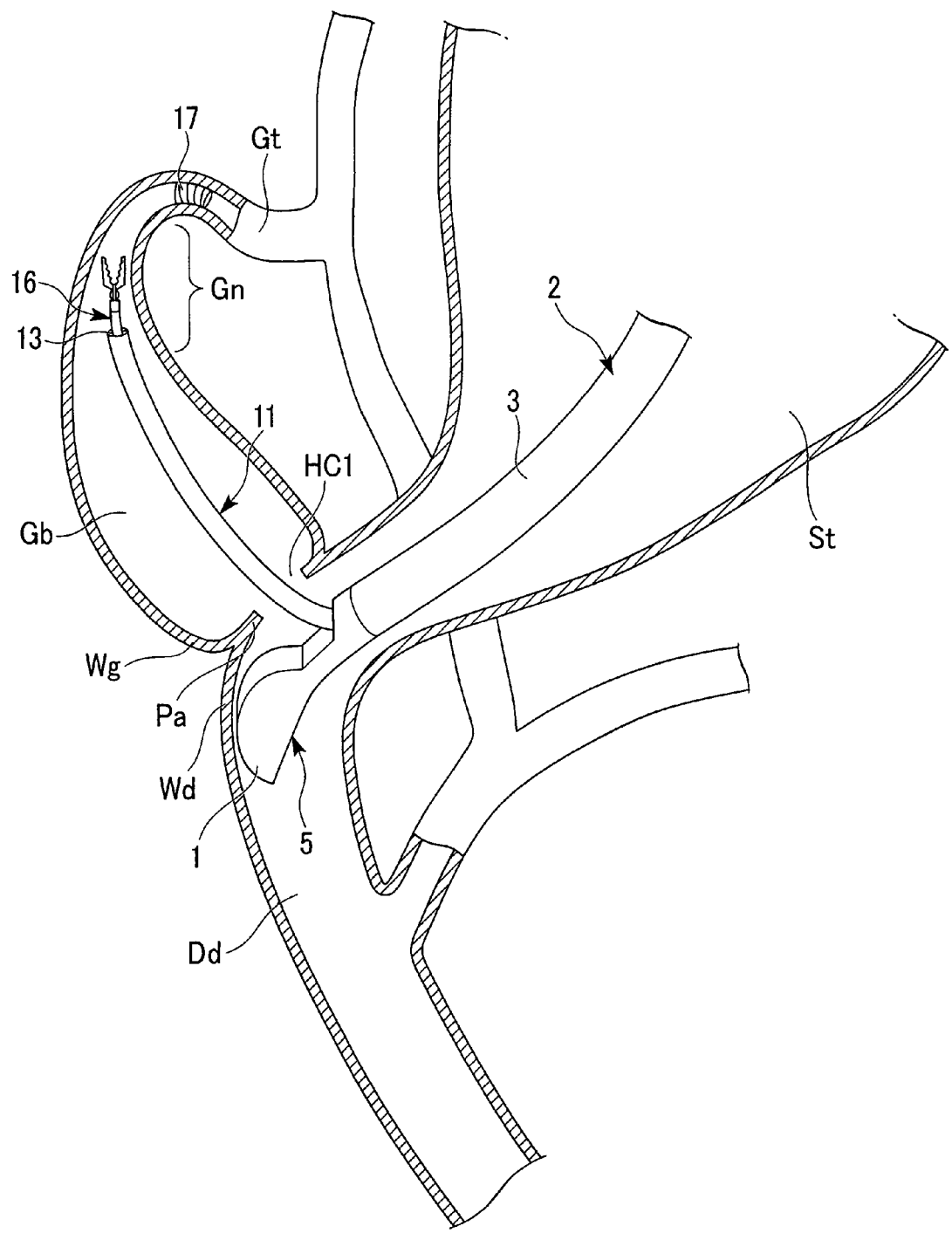
FIG. 8 shows the obstruction at the neck of gall bladder.
Figure 9:
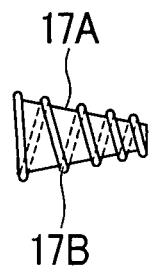
FIG. 9 shows an example of modification of plug.

As shown in FIG. 8, to obstruct the neck of gall bladder, the small endoscope 11 is delivered further into the gall bladder Gb, and the plug 17 is inserted in the entrance of the gall bladder duct Gt from the neck of gall bladder Gn using the forceps 16 which has been delivered through the instrument channel 13, then detained. Bile, which is the cause of gallstone, will no longer flow into the gall bladder Gb. FIG. 9 shows an example of modification of a plug. The plug 17A has a converging, tapered front end, and a screw 17B in the periphery protrudes. The gall bladder duct Gt can be obstructed completely and fall-off can be prevented.

Figure 10:
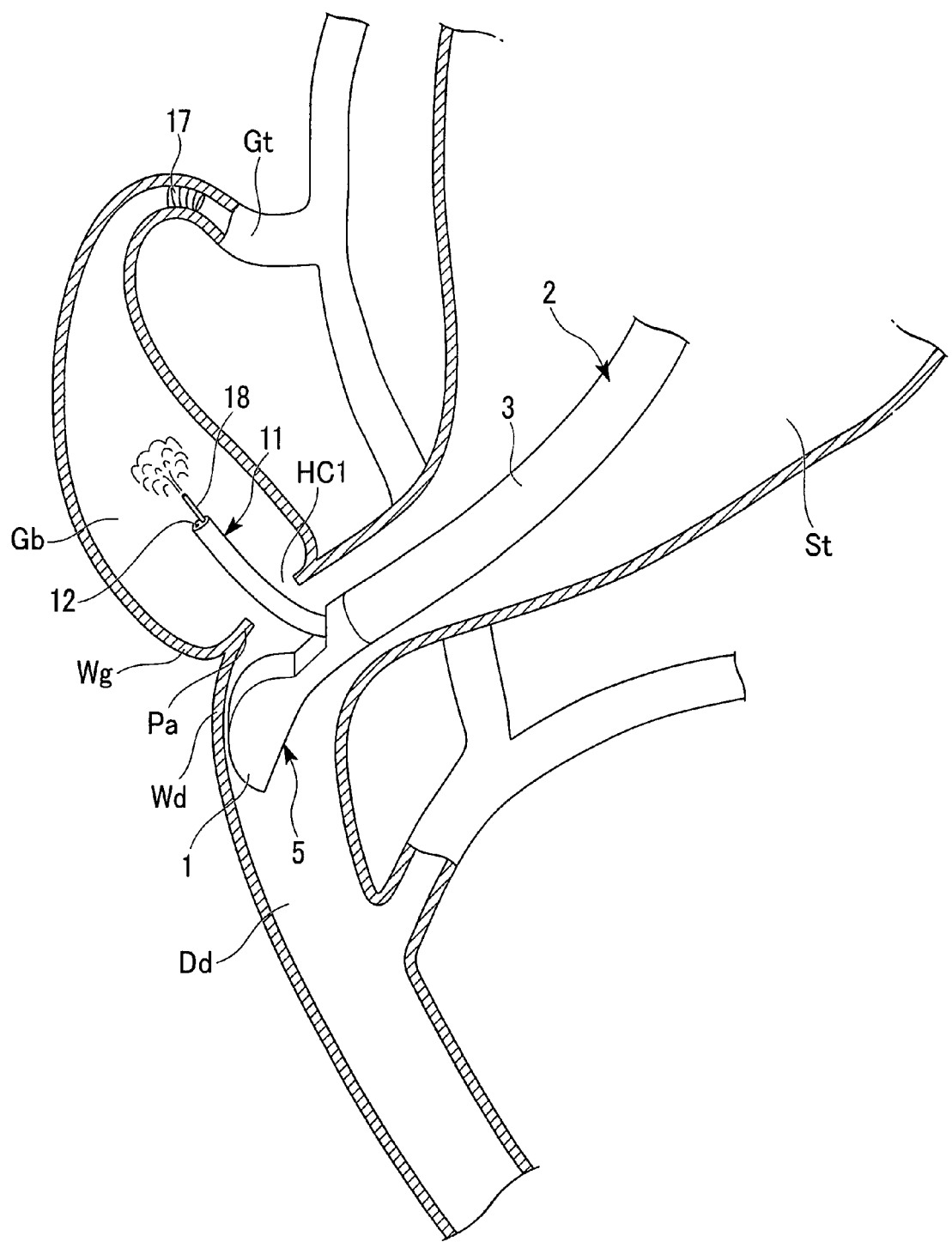
FIG. 10 shows the loss of function of the gall bladder.

When the function of the gall bladder Gb is maintained, the function of the epithelial cell is lost. As in the example of severe inflammatory condition, if the function of the gall bladder is already lost, this procedure can be omitted. As shown in FIG. 10, the small endoscope 11 is pulled back to near the puncture Hc1, and the liquid delivery tube 18 is passed into the instrument channel 13. The heated saline solution or the heated contrast agent is injected through the liquid delivery tube 18. The function of the epithelial cell is lost by thermal ablation of the heated medium. Thermal ablation may be repeated at fixed intervals, for instance a total of 3 times every other day.

Thereafter, the small endoscope 11 may be pulled out from the puncture Hc1 and the procedure is completed.

Figure 11:
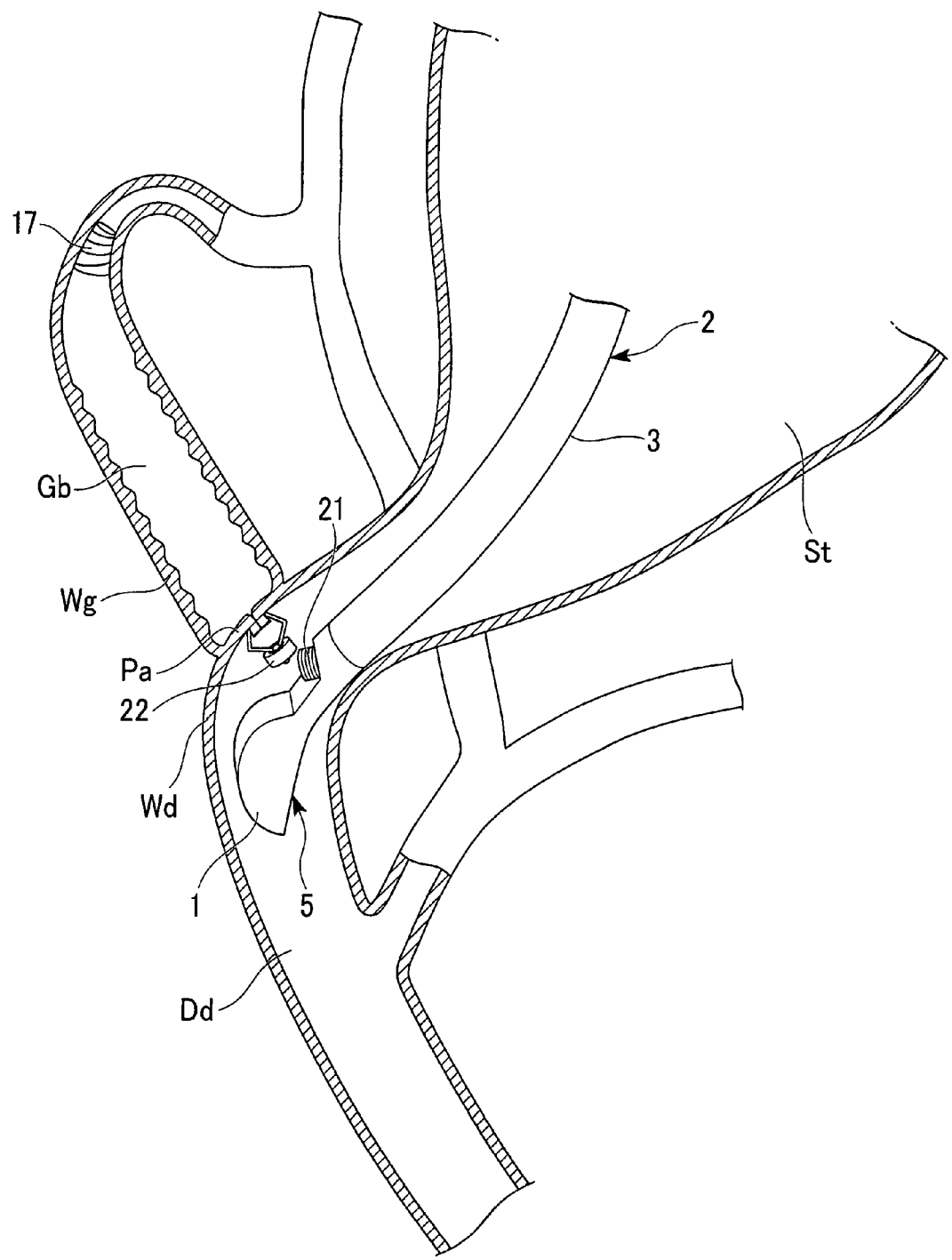
FIG. 11 shows the puncture closed by a clip.

When the thermal ablation is being performed repeatedly, or if there is no need to close the puncture Hc1, then the puncture Hc1 may be left open, but if necessary, the puncture Hc1 may be closed. For example, as shown in FIG. 11, the tissue around the puncture Hc1 may be held by the clip 22 attached to the applicator 21 through the endoscope 2, and only the clip 22 may be detained on the duodenum Dd side.

According to the present embodiment, stones in the gall bladder Gb can be extracted through the natural orifice. This procedure is superior to surgical operation from cosmetic aspects, and the pain is also diminished. Since there is no need to perform an open abdominal surgery, the cost required for the procedure can be reduced, and the procedure can be performed on elderly or obese individuals, and patients with severe complications.

According to the present embodiment, after the stones are extracted, the function of the gall bladder Gb is lost, but the gall bladder itself need not be ablated. In this case, the gall bladder Gb that has lost its function, will become atrophied with the passage of time, but blood flow will be sustained, so no side effect is likely to occur. That is, definitive therapy equivalent to that of transcutaneous cholecystectomy can be performed by endoscopic manipulation through a natural orifice.

The procedure to create obstruction at the neck of gall bladder in step S160 need not be implemented if the gall bladder function is lost and adequate atrophy can be seen.

Also, the cleaning in step S140 may be performed between step S160 and step S170. The cleaning may be performed twice or more or may be performed between step S160 and step S170 only. Moreover, there is no need to strictly define the procedure from step S140 to step S170 in the flow chart of FIG. 3; even if the steps are interchanged, the treatment is valid.

Second Embodiment

An example of modification of procedure for obstruction at the neck of gall bladder in step S160 is described here.

Figure 12:
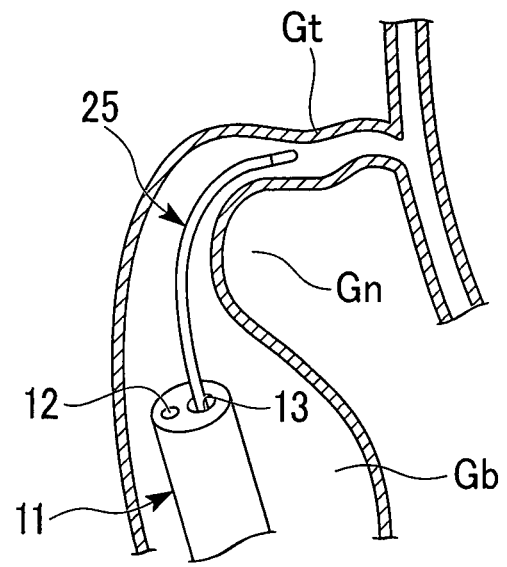
FIG. 12 shows an example of modification of procedure for obstructing the gall bladder neck portion.
Figure 13:
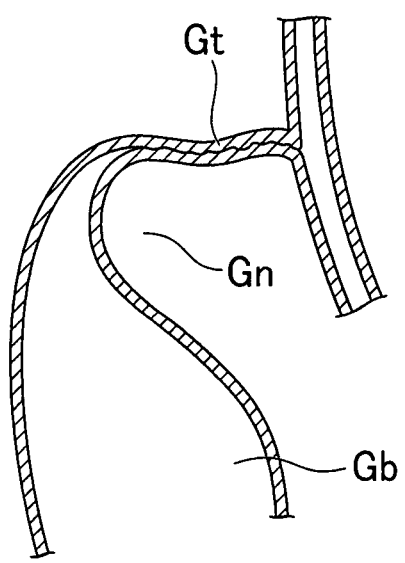
FIG. 13 shows the opening of the gall bladder duct coalesced by the procedure in FIG. 12.
Figure 14:
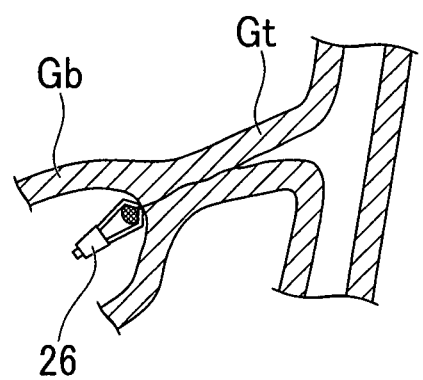
FIG. 14 shows the coalesced portion further secured by a clip.

As shown in FIG. 12, a cautery device 25 such as heat probe or electric scalpel is passed through the instrument channel 13 of the small endoscope and the gall bladder duct Gt is cauterized. As shown in FIG. 13, the tissues of gall bladder duct damaged by cauterization cause edema, coalesce thereafter, and are obstructed. Firmer obstruction can be achieved by gripping the tissues after cauterization with the clip 26, as shown in FIG. 14.

Figure 15:
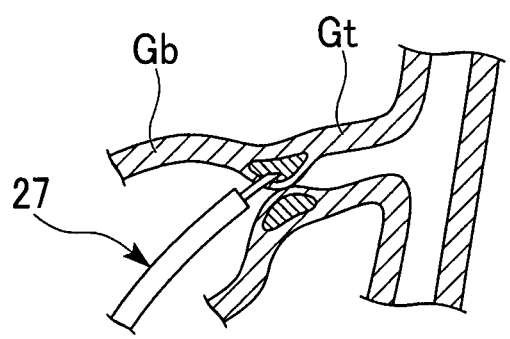
FIG. 15 shows the obstruction of a duct by injecting fluid in the gall bladder duct and distending it.

Moreover, as shown in FIG. 15, a local hypodermic needle 27 may be inserted to the subepithelial layer of the gall bladder duct Gt, and collagen and so on may be injected to distend the tissue to obstruct the gall bladder duct Gt. The fluid injected in the tissue may be any fluid that does not have adverse effects on the living bodies; it is not limited to collagen only.

Other procedures such as suturing or dispersing inflammatory substance to cause edema and coalescing the tissues may also be performed.

Third Embodiment

An example of modification of thermal ablation performed as part of the procedure for loss of function of the gall bladder Gb in step S170 is described here.

Figure 16:
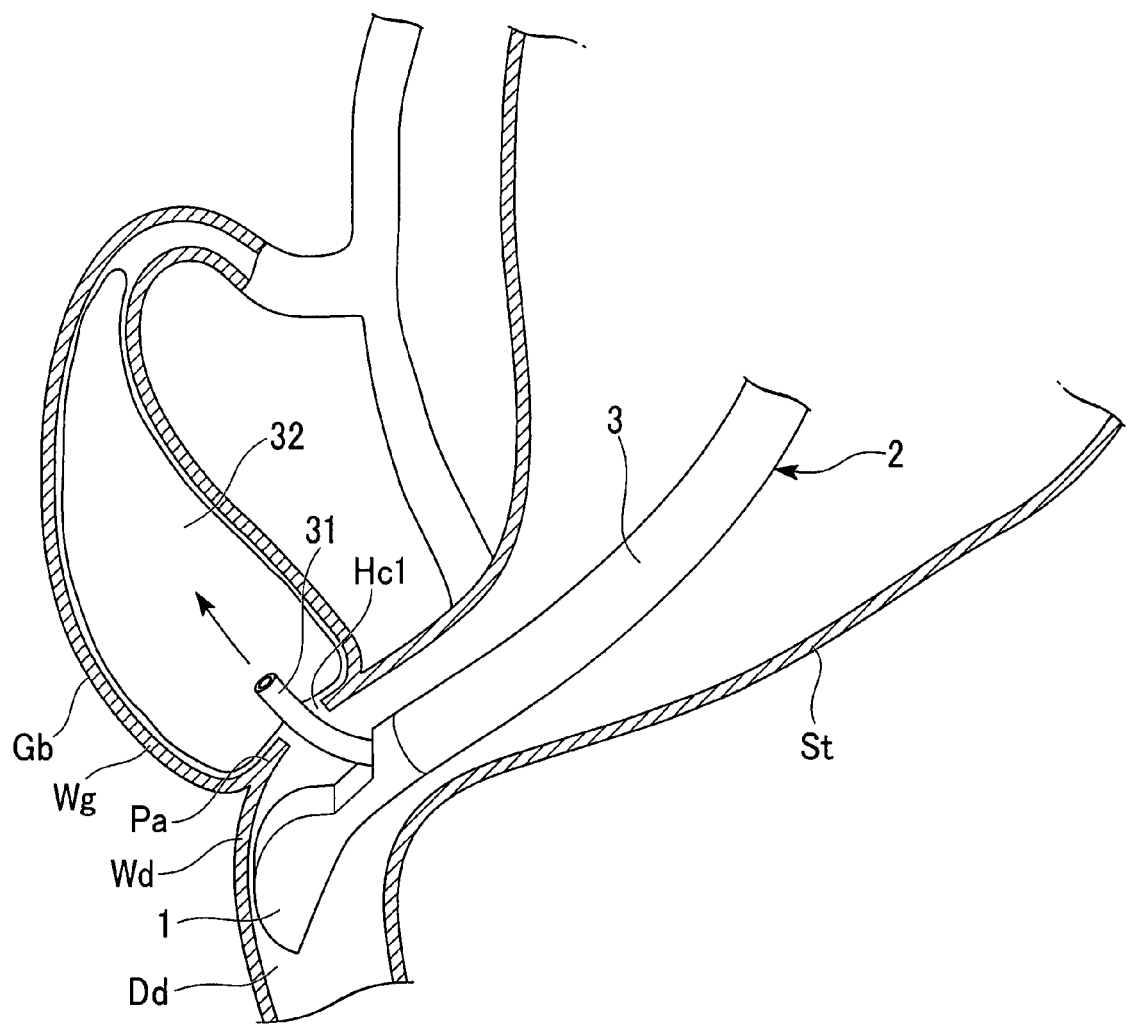
FIG. 16 shows an example of modification of procedure that causes loss of function of gall bladder.

As shown in FIG. 16, the liquid delivery tube 31 is passed through the puncture Hc1 from the endoscope 2 and introduced into the gall bladder Gb. Heated saline solution is injected into a balloon 32 attached to the front end of the liquid delivery tube 31. The balloon 32 swells along the wall face of the gall bladder Gb. The function of the gall bladder Gb is lost to the epithelial cell by uniform transmission of heat to the epithelial cell from the saline solution through the balloon 32. The fluid heated within the balloon 32 may be heated contrast agents or a gas at high temperature.

A cautery device such as a device that radiates high frequency, laser or microwaves may be passed through the instrument channel 13 of the small endoscope 11, the epithelial cell of the gall bladder Gb may be cauterized and the function may be lost; similar effects may be anticipated from this procedure also.

Fourth Embodiment

Chemical ablation is described here as an example of modification of procedure for loss of function of the gall bladder Gb in step S170.

When performing chemical ablation similar to FIG. 5, a tube is introduced in the gall bladder Gb, and ethanol or a medicinal agent may be injected in the gall bladder Gb, and the function of the epithelial cell is lost. The small endoscope 11 introduced in the gall bladder Gb, as shown in FIG. 6, may also be used. Even when chemical ablation is adopted, it may be repeated at fixed intervals, for instance a total of 3 times every other day.

Fifth Embodiment

As an example of modification of the first embodiment, the case of performing procedure from steps S150 to S170 wherein the endoscope 2 is advanced into the gall bladder Gb, is described here.

Figure 17:
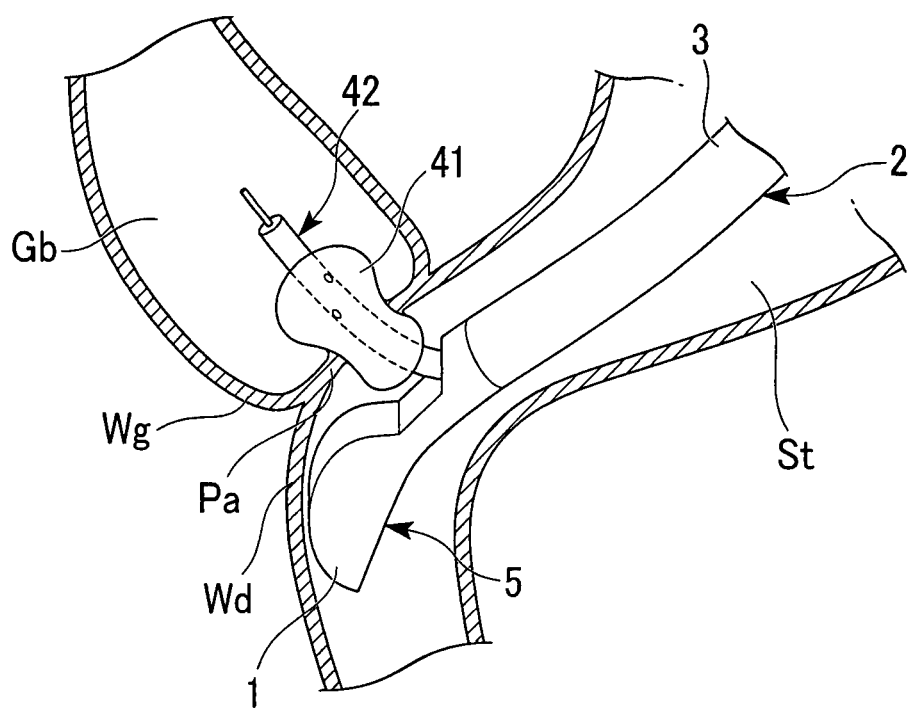
FIG. 17 shows the procedure for dilation of puncture.
Figure 18:
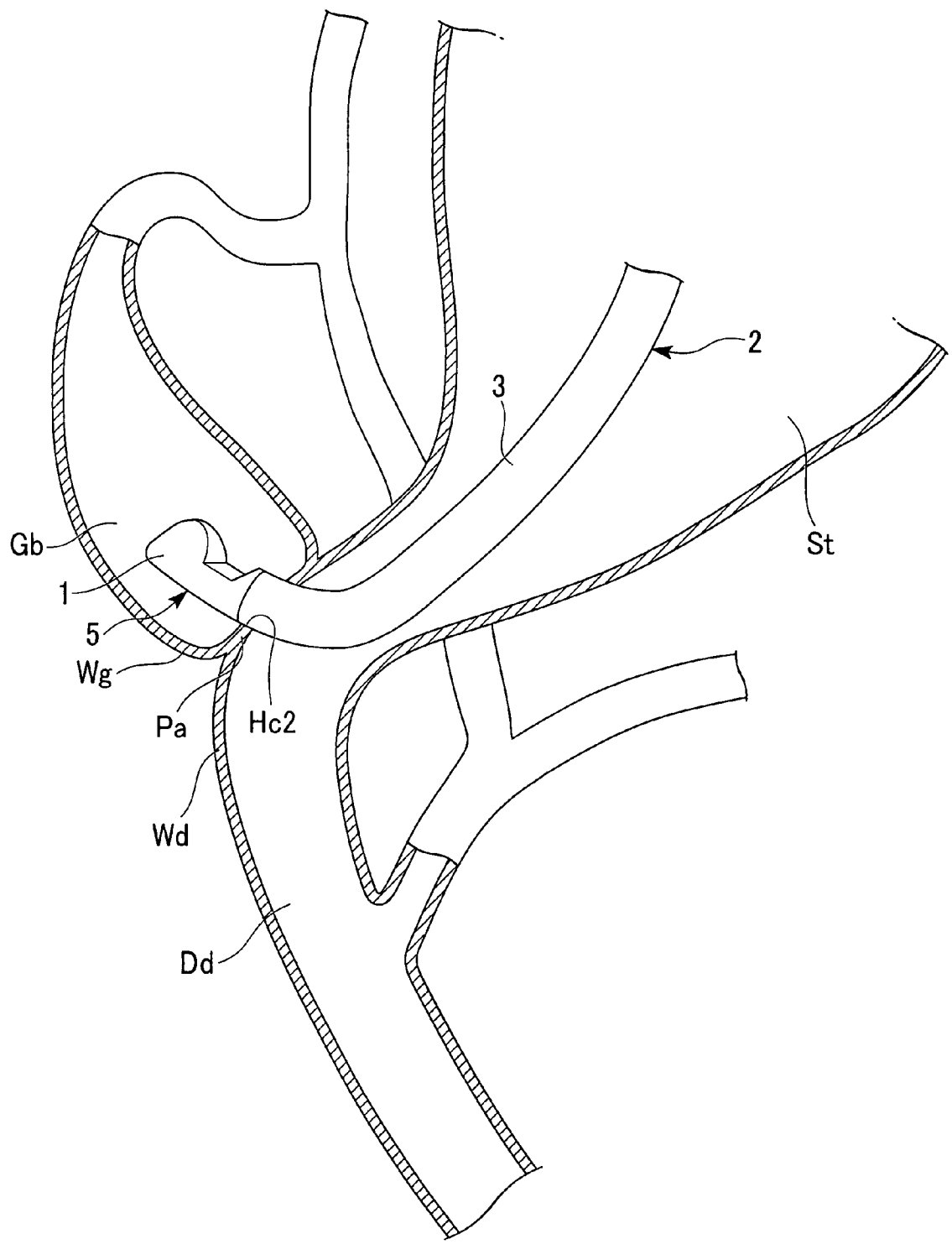
FIG. 18 shows the introduction of an endoscope into the gall bladder from the dilated puncture.

When puncture Hc1 is formed in the coalesced portion Pa of the gall bladder Gb, the puncture Hc1 is dilated so that the endoscope 2 can be inserted. As shown in FIG. 17, a incising device 42, such as the high-frequency knife fitted with a balloon 41 may be used. When the puncture Hc1 is created, the incising device 42 is delivered from the endoscope 2 up to the fitted position of the balloon 41. Fluid is dispensed from the proximal side to the operator and the balloon 41 is inflated so that the puncture Hc1 is pressed and widened, and an area of puncture enabling insertion of the endoscope 2 is ensured. Thereafter, the small endoscope 2 is introduced in the gall bladder Gb, as shown in FIG. 18.

Figure 19:
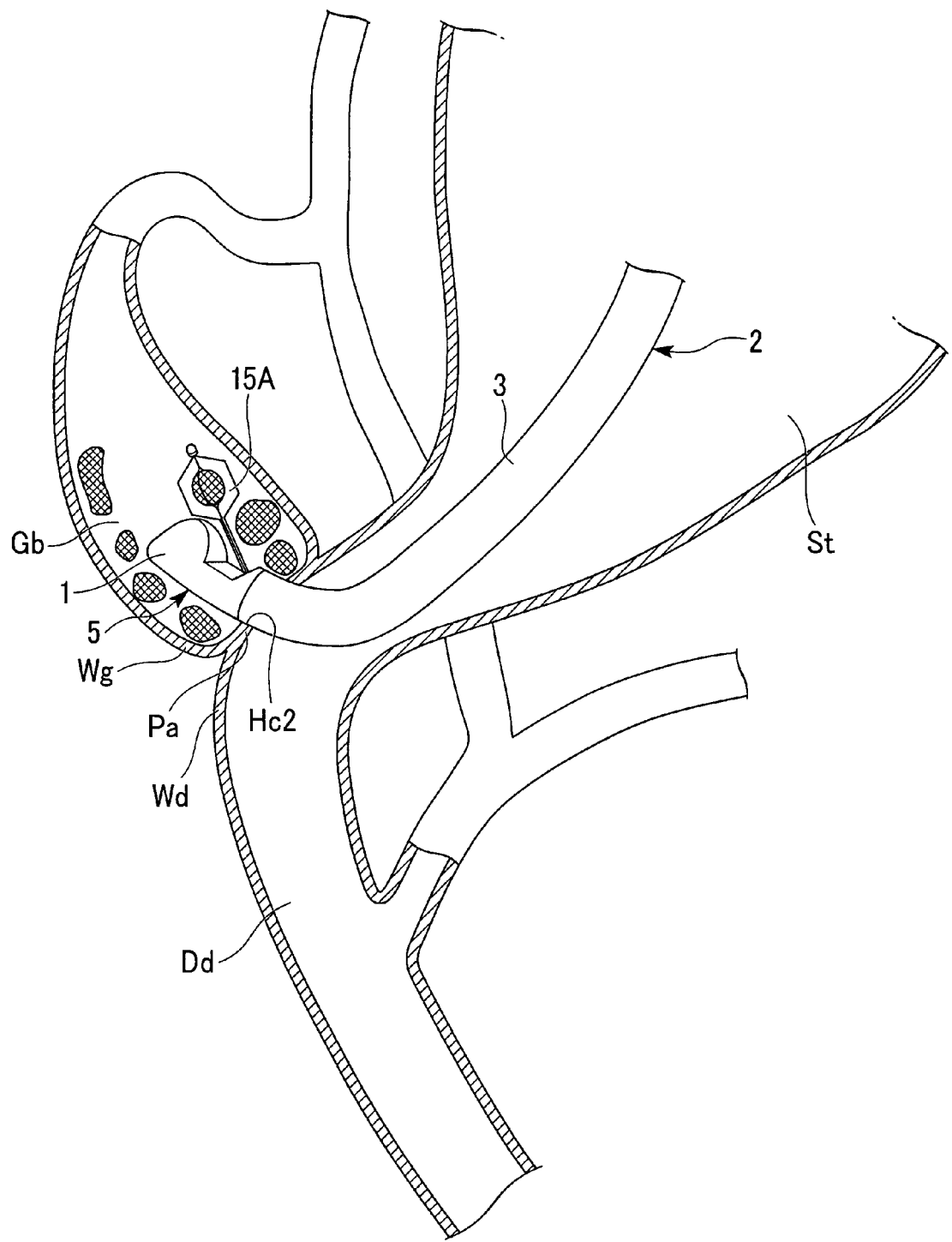
FIG. 19 shows the extraction of stones by a stone removal tool through an endoscope.

As shown in FIG. 19, stones can be extracted by the stone removal tool 15A through the instrument channel.

Figure 20:
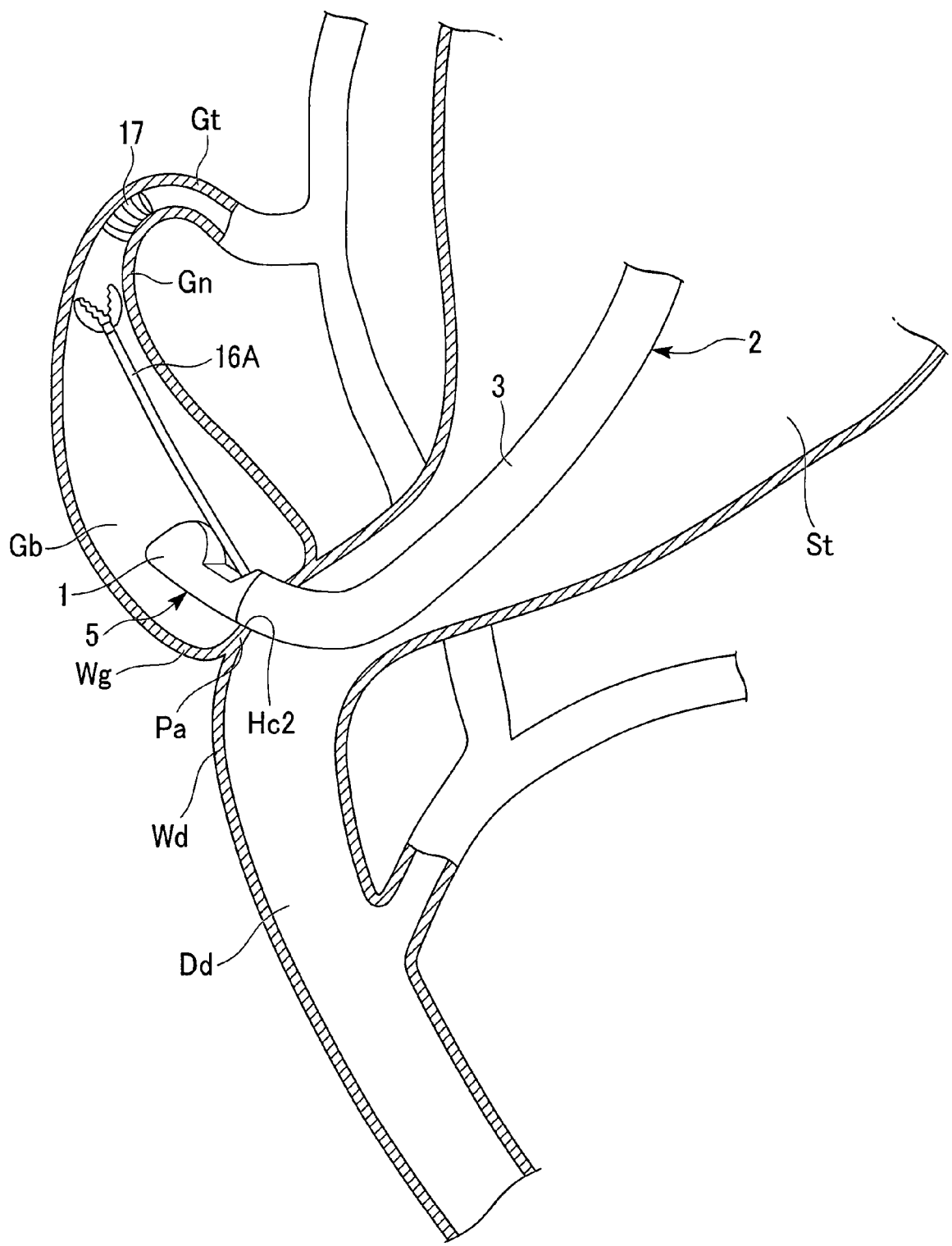
FIG. 20 shows the embedding of a plug using forceps through an endoscope.

When the neck of gall bladder Gn is obstructed, as shown in FIG. 20, the plug 17 is embedded directly from the endoscope 2 with the forceps 16A. Other procedures described in the second embodiment may also be adopted.

Figure 21:
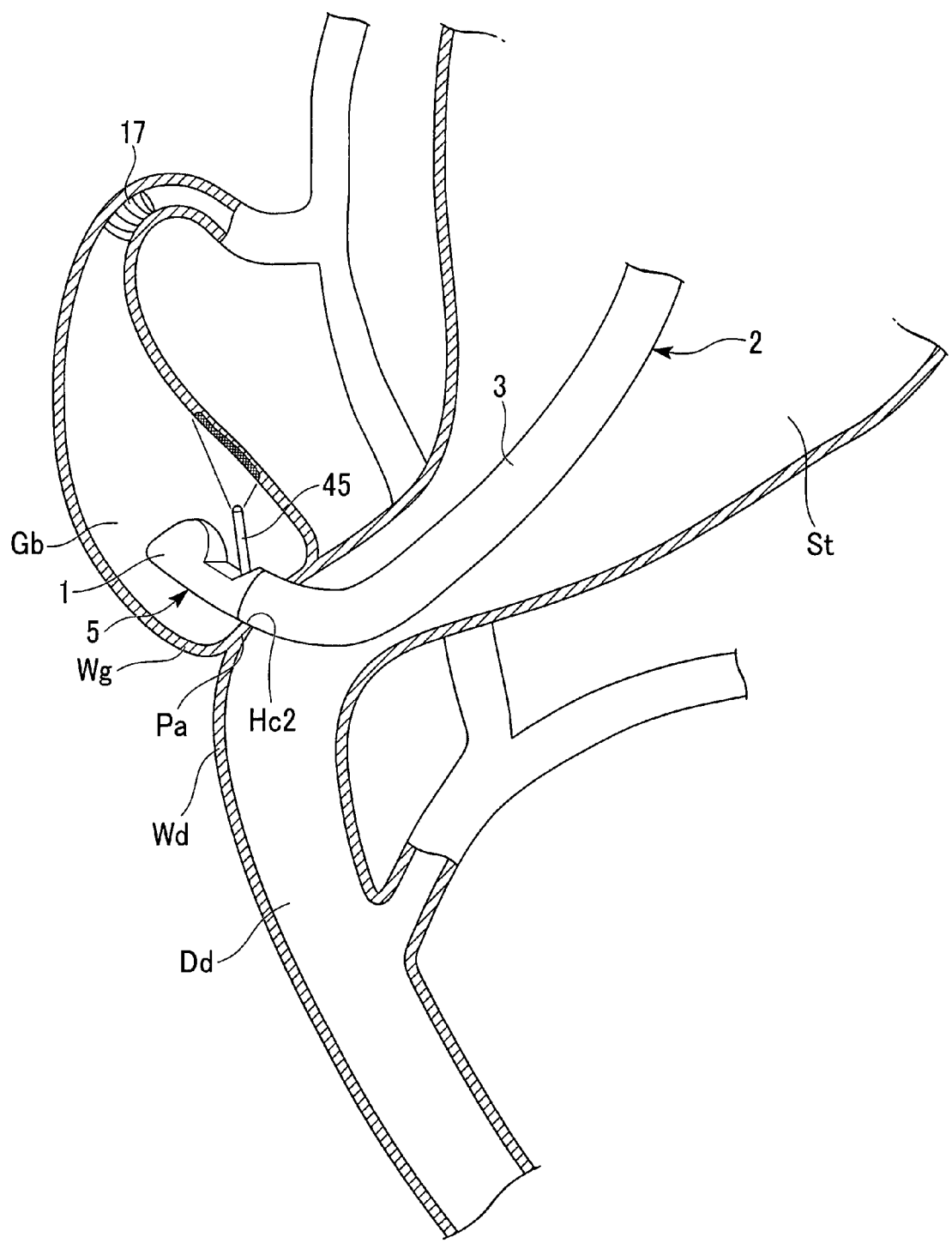
FIG. 21 shows the loss of function of the gall bladder using a probe through an endoscope.

As shown in FIG. 21, laser probe 45 is passed through the endoscope 2, the epithelial cell is cauterized, and the function of the gall bladder Gb is lost. The area on which the laser is irradiated loses its function since the epithelial cell suffers thermal denaturation. Other cautery devices such as high-frequency knife or device that radiates microwaves may be used.

According to the present embodiment, effects similar to the first embodiment can be obtained without using the small endoscope.

In a certain part of the procedure, the small endoscope 11 may be used, while the endoscope 2 may also be used in the remaining procedure.

Sixth Embodiment

Figure 22:
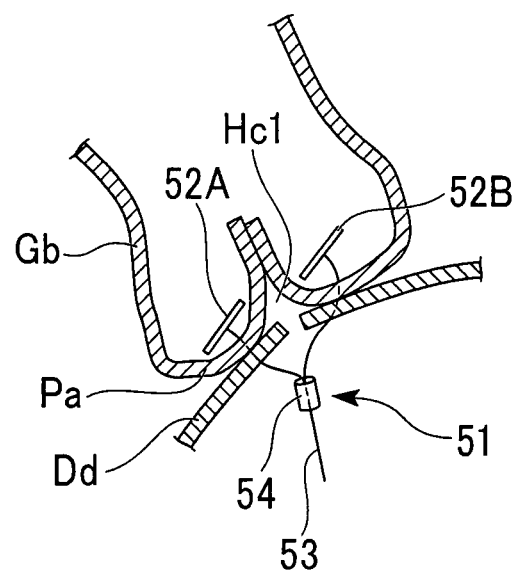
FIG. 22 shows the puncture closed by a detention tool.

To describe an example of modification of procedure to close puncture Hc1 (or puncture Hc2), a suture tool 51 as shown in FIG. 22 may be used to close the puncture Hc1. The suture tool 51 is configured with two anchors 52A and 52B connected by a suture thread 53, and a stopper 54 that can fasten a tissue.

When the puncture Hc1 is closed, a puncture needle passed through the endoscope 2 is made to penetrate the coalesced portion Pa around the puncture Hc1, and the anchor 52A housed inside the puncture needle is pushed into the gall bladder Gb. Since one end of the suture thread 53 is attached to the anchor 52A, if the puncture needle is pulled out from the coalesced portion Pa, and the suture thread 53 penetrates the coalesced portion Pa. The anchor 52A is adequate larger in size than the suture thread 53; therefore, it remains in the gall bladder Gb. Similarly, the anchor 52B attached to the other end of the suture thread 53, is detained on the gall bladder Gb side using the suture needle. The detention position of the second anchor 52B is on the opposite side of the first anchor 52A with the puncture Hc1 sandwiched between the two anchors. When the suture thread 53 is pulled so as to push the stopper 54 passed through the suture thread 53 is pressed against the tissue, then the puncture Hc1 is closed.

Seventh Embodiment

The present embodiment relates to the procedure for completing a one-time treatment and is performed when the alimentary tract walls such as those of the gall bladder Gb and the duodenum Dd have not been coalesced. In the procedure according to the present embodiment, since, the duodenum and the gall bladder are generally not coalesced, it is important to approach to the internal part of gall bladder from the duodenum to the gall bladder without leaking the fluid (bile) into the abdominal cavity.

Figure 23:
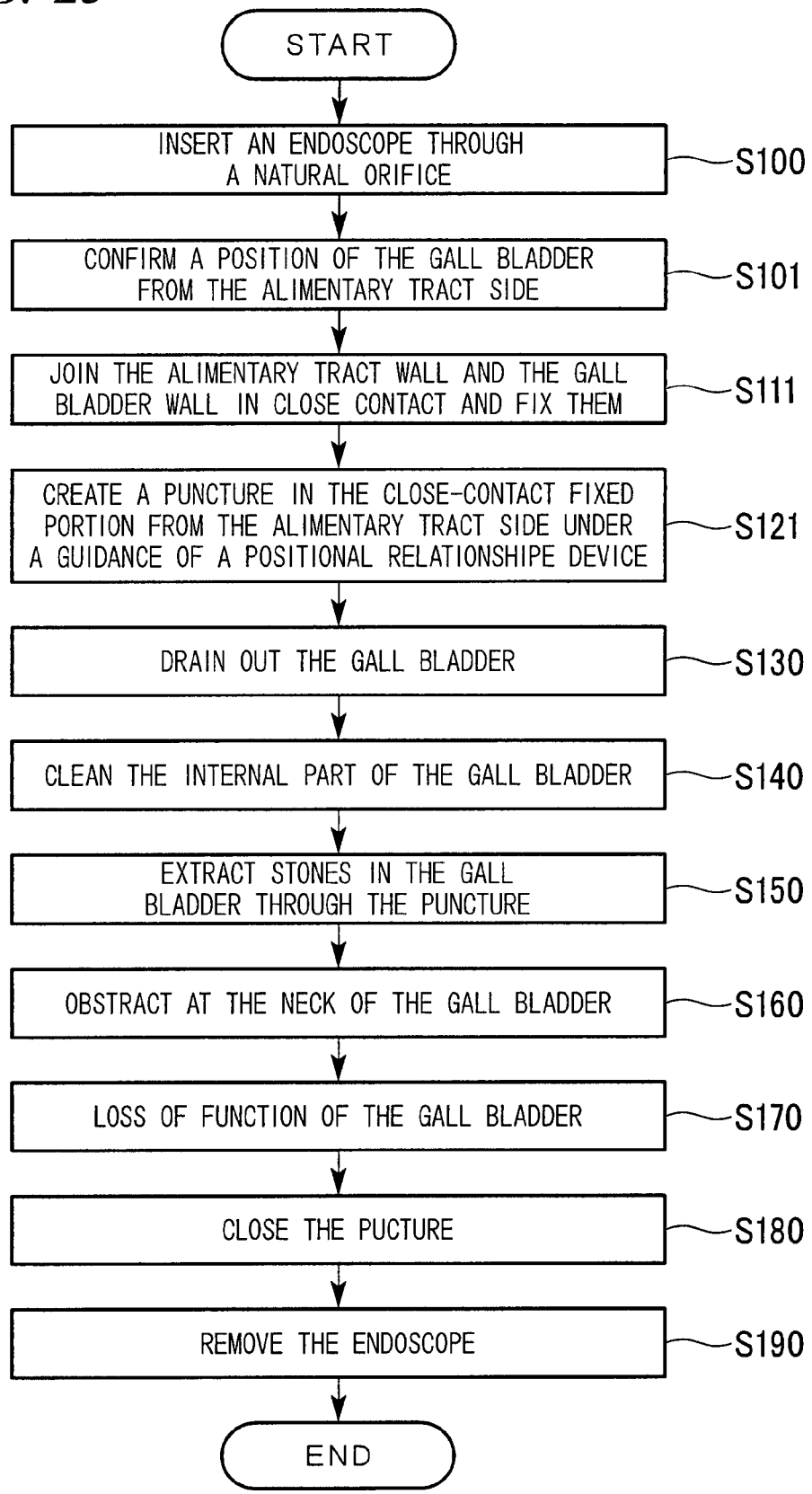
FIG. 23 shows a flow chart describing the procedure of the seventh embodiment.

FIG. 23 shows the flow chart for procedure in the present embodiment. First, the endoscope 2 is inserted through a natural orifice (step S100), and the position of the gall bladder Gb is confirmed from the alimentary tract side (step S101). A close-contact fixed portion between the alimentary tract wall and the gall bladder wall Wg is formed (step S111), and puncture is formed in the close-contact portion (step S121) from the alimentary tract side under the guidance of the positional relationship device. The gall bladder Gb is drained out (step S130) and subsequently, the internal part of the gall bladder Gb is cleaned (step S140). Stones in the gall bladder Gb are extracted through the puncture (step S150) and the neck of gall bladder Gn is obstructed (step S160). After the loss of function of the gall bladder Gb (step S170), the puncture is closed (step S180), and the endoscope 2 is removed (step 190).

Figure 24:
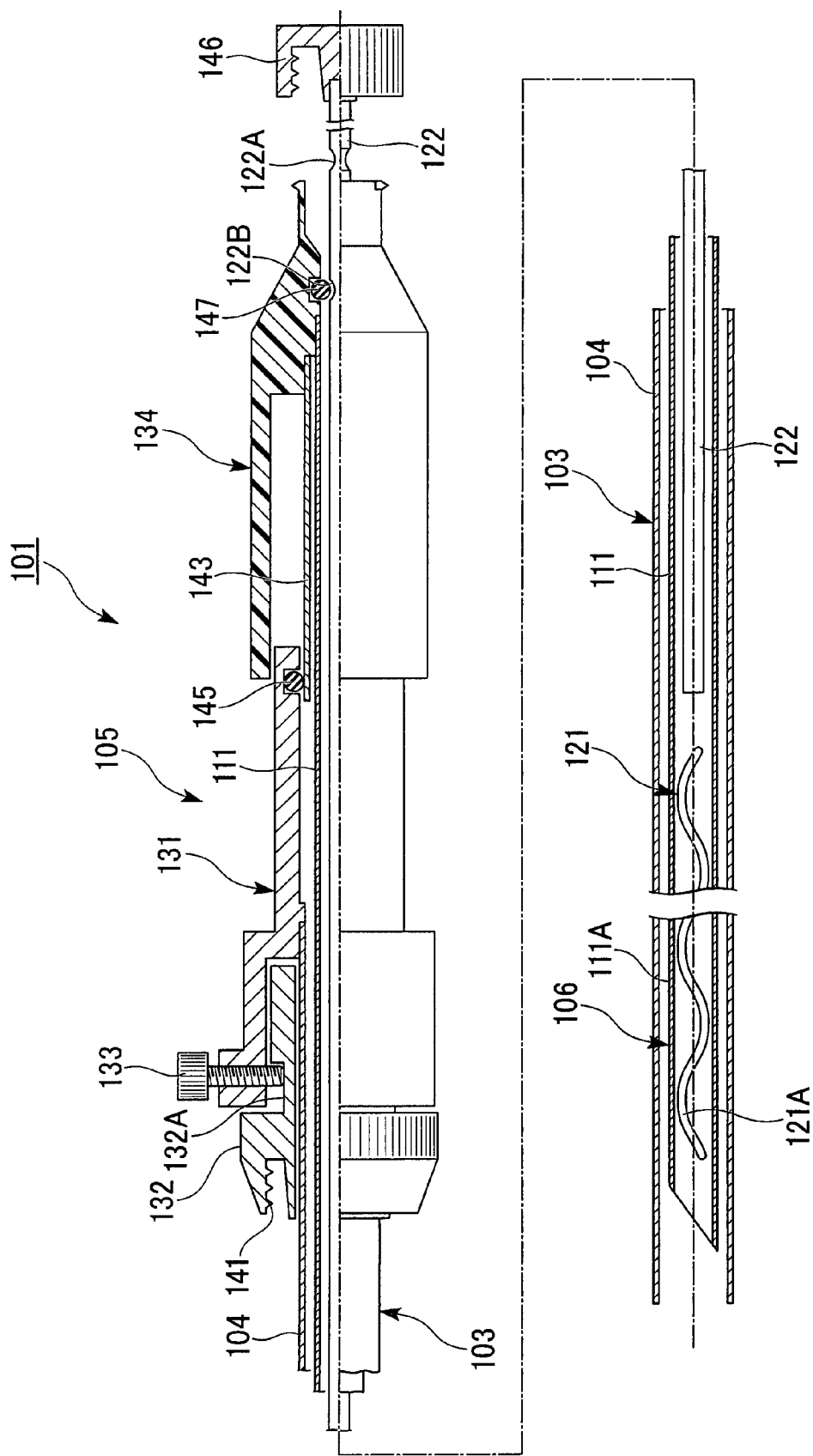
FIG. 24 is a cross sectional view showing the applicator configuration.
Figure 25:
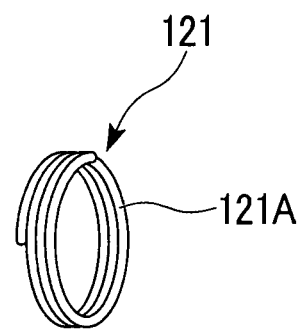
FIG. 25 is an external view of the tissue fastening tool.

An applicator 101, as shown in FIG. 24, can be used in the procedure for forming a close-contact fixed portion the alimentary tract wall and the gall bladder wall in step S111. This applicator 101 is used by passing it through the instrument channel of the flexible endoscope 2 inserted via the patient's mouth. The endoscope 2 should preferably be an ultrasonic endoscope, but another device for understanding the positional relationship, as mentioned above, may be used together with the endoscope. A tissue fastening tool 121 detained in the body by the applicator 101 is housed in a deployed section 111A in the substantially extended condition. As shown in FIG. 25, the tissue fastening tool 121 has a coil shape when in the no-load condition. If it is taken out of the deployed section 111A, it returns to its original coil shape by its self-restoring force. In this tissue fastening tool 121, a tightly wound coil spring made of a superelastic alloy such as NiTi may be used. The coil spring is not limited to a tightly wound spring; the winding may be appropriately set according to the thickness of the tissue to be held by the coil and the spring force required.

First, the condition outside the duodenum Dd is examined by the ultrasonic probe 1, and an appropriate location for procedure is searched proximally to the gall bladder Gb.

Figure 26:
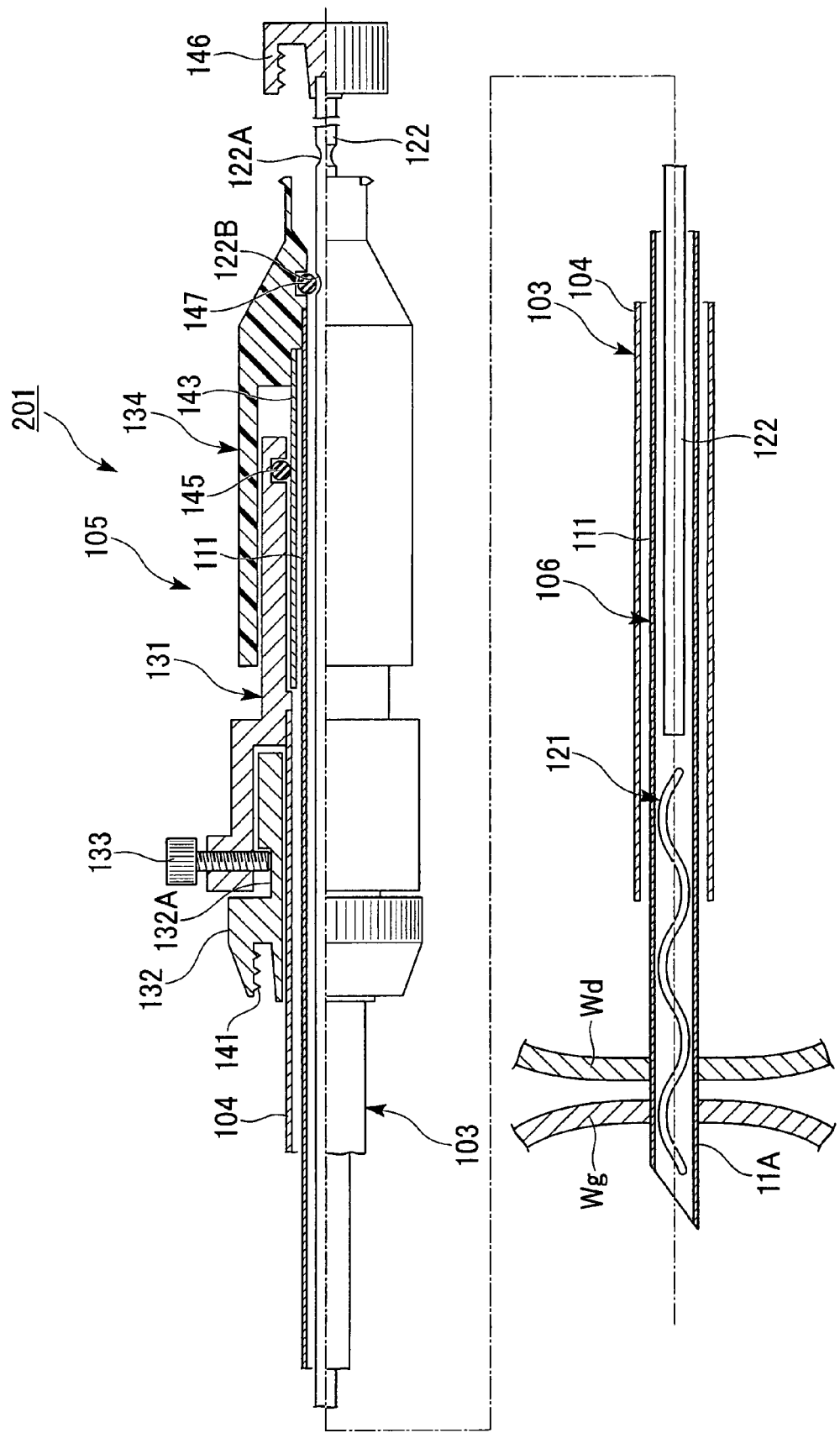
FIG. 26 shows the penetration of a tissue protruded by the deployed section from the front end of an applicator.

The applicator 101 passed through the instrument channel is advanced, and it is protruded toward the lateral direction from the forceps elevator 6. As shown in FIG. 26, the slider 134 of the operation part 105 is pushed into the operation part body 131. The needle tube 111 fixed in the slider 134 advances, and the deployed section 111A protrudes from the front end of the sheath 104. Since the second groove 122B is joined to the slider 134 through the O-ring 147, the stylet 122 advances together with the needle tube 111. As a result, the deployed section 111A passes completely through from the inside to the outside of the duodenum wall Wd, and furthermore, passes through from the outside to the inside of the gall bladder wall Wg.

Figure 27:
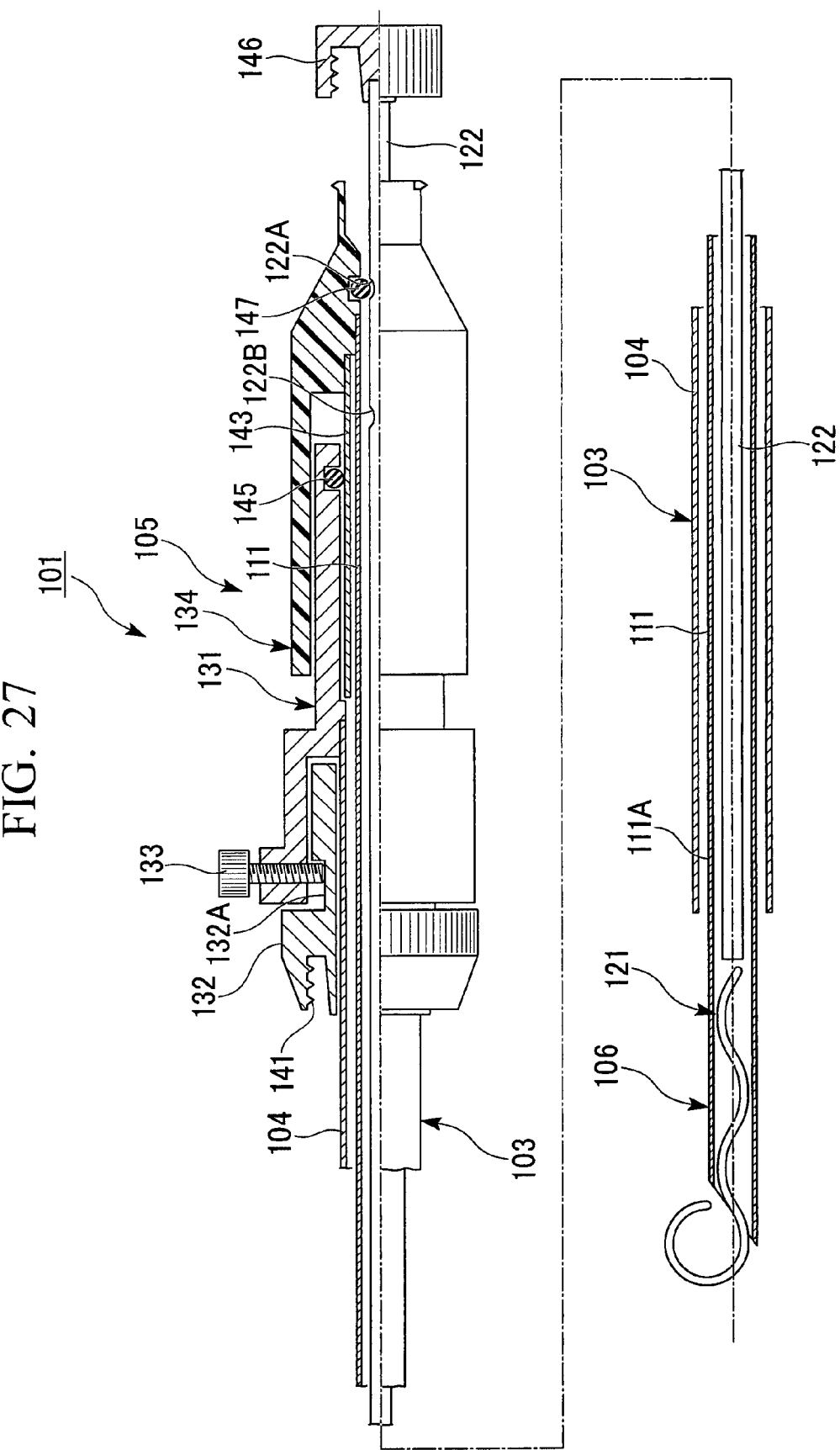
FIG. 27 shows the view when the stylet has been advanced to push out the tissue fastening tool halfway.
Figure 28:
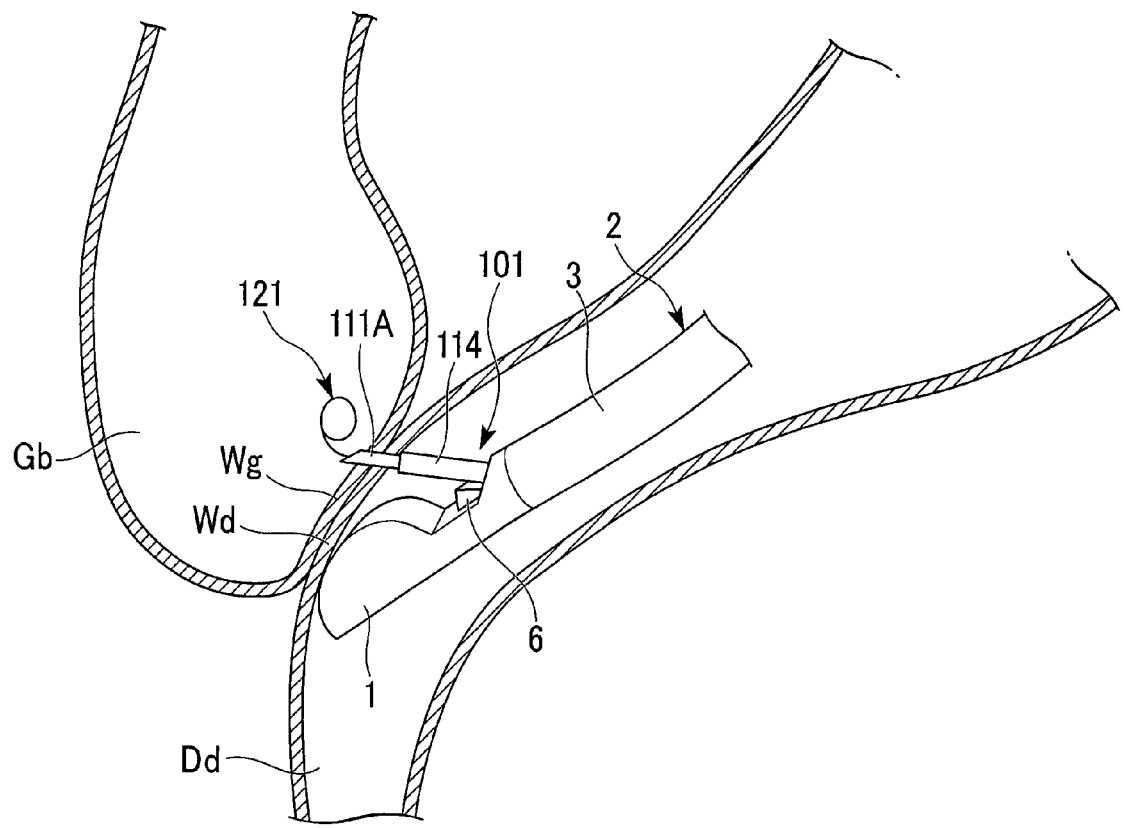
FIG. 28 shows the tissue fastening tool pushed out halfway with its original coil shape restored.

As shown in FIG. 27, the first groove 122A is joined by friction with the O-ring 147 by further pushing the stylet knob 146. The stylet 122 pushes out the tissue fastening tool 121 into gall bladder Gb from the front end opening of the deployed section 111A. The push-out extent at this stage is substantially equal to the distance of shift of the stylet knob 146 on the proximal side to the operator, and has a length equivalent to substantially half the total length of the tissue fastening tool 121. As shown in FIG. 27 and FIG. 28, a part of the tissue fastening tool 121 pushed into the gall bladder Gb restores itself into coil shape simultaneously as it is pushed because of its superelasticity.

Thereafter, the applicator 101 is retracted, the deployed section 111A is pulled out from the gall bladder Gb, and is pulled back into the duodenum Dd. The tissue fastening tool 121 with its original coil shape restored, is in contact with the inside wall of the gall bladder Gb. If a gap exists between the gall bladder Gb and the duodenum Dd, the tissue fastening tool 121 in the gall bladder Gb becomes an anchor, the gall bladder is pulled up to the duodenum Dd and comes in close contact with it.

Figure 29:
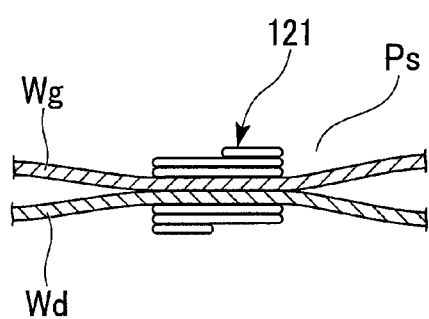
FIG. 29 shows the gall bladder fixed to the duodenum by the tissue fastening tool with its original coil shape restored.
Figure 30:
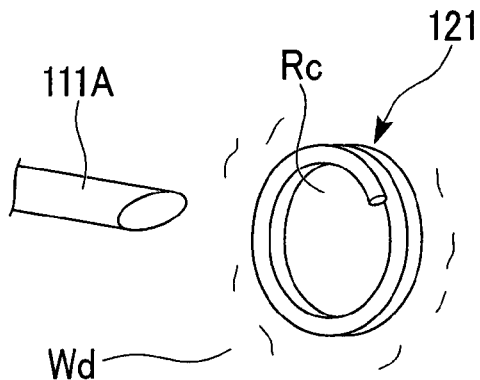
FIG. 30 shows the closed space fastened by the tissue fastening tool.

The stylet knob 146 is advanced further, and the remaining part of the tissue fastening tool 121 is pushed out from the deployed section 111A with the stylet 122. The tissue fastening tool 121 is completely released from the applicator 101. As shown in FIG. 29, a part of the tool on the duodenum Dd side also exhibits the superelasticity so that it restores itself into coil shape simultaneously when it is pushed out. As a result, the duodenum wall Wd and the gall bladder wall Wg are fastened by the tissue fastening tool 121 and comes in close-contact. As shown in FIG. 29 and FIG. 30, the tissue fastening tool 121 is detained in coil shape both on the duodenum Dd side and the gall bladder Gb side, that is, when viewed from the axial direction of the coil, it is detained in an annular contact condition with the tissue. Thus a close-contact fixed portion Ps is formed between the duodenum wall Wd and the gall bladder wall Wg by the tissue fastening tool 121.

Figure 31:
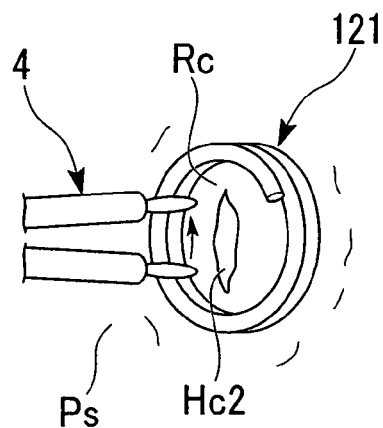
FIG. 31 is an explanatory diagram of procedure for extending the puncture with a high-frequency knife.

Next, the close-contact fixed portion Ps is incised, and a puncture is formed. As shown in FIG. 31, the incising device 4 is used in the closed area Rc formed by the tissue fastening tool 121 within the close-contact fixed portion Ps, and puncture Hc2 is formed. First, a through hole may be created in the area Rc with the deployed section 111A, as shown in FIG. 30. Thereafter, the puncture may be extended using the incising device 4.

By performing the procedure mentioned above, approach from the internal part of the duodenum to the internal part of the gall bladder can be made safely and easily without any leakage of the bile.

In this way, steps S130 to S170, namely cleaning within the gall bladder Gb, extraction of stones, obstruction at the neck of gall bladder Gn, and stopping the function of the gall bladder Gb, may be implemented if necessary through the puncture formed in the close-contact fixed portion Ps. Moreover, these procedures need not be strictly defined; even if the steps are interchanged, the treatment remains valid. The procedure within the gall bladder Gb is performed by a method similar to the method explained in a previous embodiment, that is, by inserting the tube, inserting the small endoscope 11, and so on.

Thereafter, devices such as the small endoscope 21 may be pulled out from the puncture Hc2, and the puncture Hc2 is closed. As shown in FIG. 11 and FIG. 22, clip 22 or suturing tool 51 may also be used in the suturing method. Other publicly known suturing instruments or clips may be used. Thereafter, the endoscope 2 is removed from the patient.

According to the present embodiment, effects similar to the first embodiment can be obtained by a one-time treatment when the gall bladder Gb is not coalesced with the duodenum Dd. By using the applicator 101, the close-contact fixed portion Ps can be easily formed. The physical burden on a patient has been large by surgical suturing under the conventional open abdominal surgery. There is a risk of leaking the bile into the abdominal cavity, and causing a serious side effect called bile peritonitis. According to the present invention, since the gall bladder and the duodenum are closely fastened, bile does not leak out to the abdominal cavity. Accordingly, there is no concern of bile peritonitis to occur.

Also, after performing steps up to step S170, the step S170 may be implemented again after a fixed interval (period). Naturally, step S180 alone may also be performed.

Instead of closing the puncture Hc2, the puncture Hc2 may be left open. The puncture Hc2 in this case is anticipated to have a long term patency. In the conventional procedure for inserting stent, a foreign object was detained in the body; therefore, as early as one month, and latest by three months to about six months, the internal hole for the stent becomes occluded and bile can no longer be drained. Thus, regular stent replacement was necessary, placing a heavy burden on patients. According to the present embodiment, the bypass hole through which the bile flows out does not clog easily because it is a luminal tissue.

Figure 32:
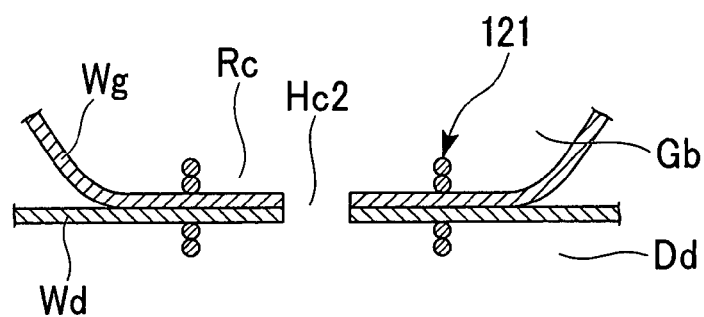
FIG. 32 is a cross sectional view of a puncture.
Figure 33:
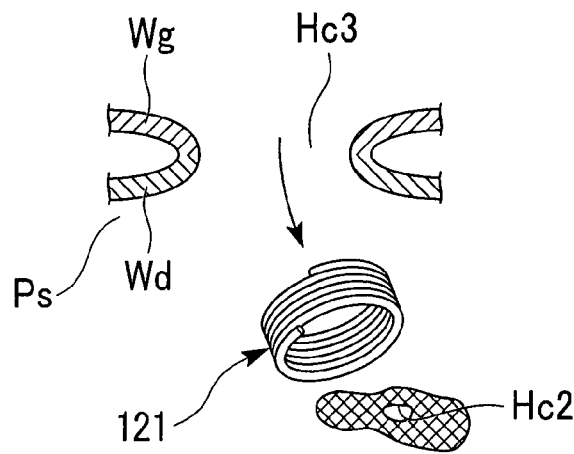
FIG. 33 shows the fallen-off tissue fastened by the tissue fastening tool.

In cases where the puncture Hc2 is left open, eventually a fistulous opening can be formed in the close-contact fixed portion Ps. In this case, when the puncture Hc2 is closed, a tissue fastening tool 121 or a suturing tool 51 is used to fasten the tissue so that the tissue surrounding the puncture Hc2 becomes the ischemic condition. For example, as shown in FIG. 32, the tissue within the area Rc is made to be the ischemic condition by the tissue fastening tool 121. With the passage of time, the area around the tissue fastening tool 121 becomes coalesced, and moreover, as shown in FIG. 33, the tissue becomes necrotized and falls off. Consequently, a fistulous opening Hc3 is formed in the close-contact fixed portion Ps. The fallen-off tissue and the tissue fastening tool 121 are spontaneously discharged from the body through the duodenum Dd. Until the tissue is necrotized, the fastened area between the duodenum wall Wd and the gall bladder wall Wg coalesce; therefore, the gall bladder Gb does not separate and does not become misaligned with respect to the duodenum Dd. Since the tissue fastening tool 121 falls off and the bypass hole becomes larger, a longer period of patency may be anticipated.

As for the subsequent procedures, procedure for losing the function of the gall bladder Gb may be additionally implemented, and endoscope 2 may be inserted and fistulous openings may be closed using a suture instrument, as shown in FIG. 11 and FIG. 22.

Eighth Embodiment

An example of modification of procedure for forming a close-contact fixed portion between the duodenum wall Wd and the gall bladder wall Wg in step S111 is described here.

Figure 34:
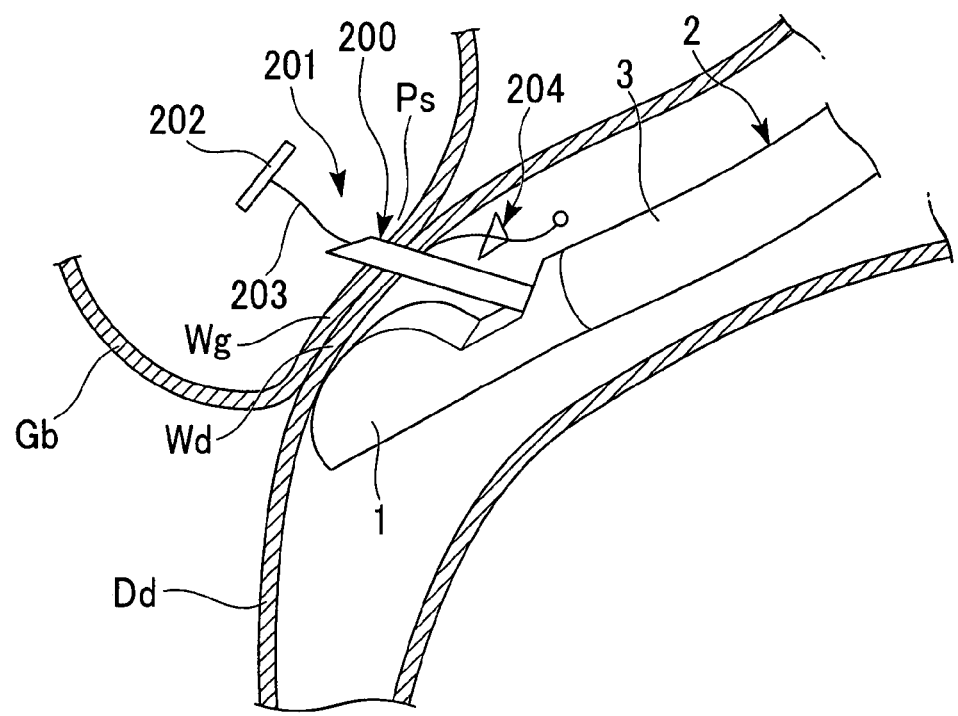
FIG. 34 shows an anchor driven into the gall bladder from the duodenum side.

As shown in FIG. 34, a puncture needle 200 is made to penetrate from the duodenum Dd into the gall bladder Gb, and an anchor 202 of a detention tool 201 housed in the puncture needle 200 is pushed into the gall bladder Gb. Since one end of the suture thread 203 is attached to the anchor 202, when the puncture needle 200 is pulled out from the gall bladder wall Wg and the duodenum wall Wd, the suture thread 203 penetrates the tissue. The anchor 202 remains in the gall bladder Gb because it is much larger in size than the suture thread 203. A stopper 204 is passed through the other end of the suture thread 203.

Figure 35:
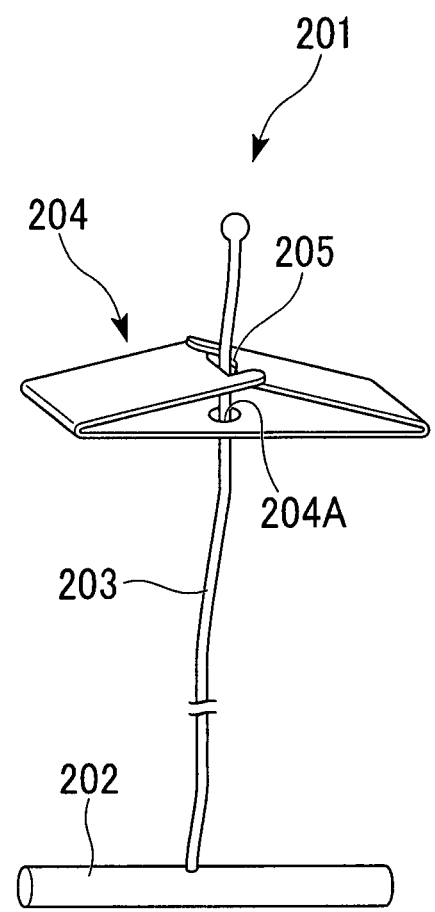
FIG. 35 is an external view of the suture tool.

As shown in FIG. 35, the stopper 204 is formed into a triangular shape by bending a sheet. A slit 205 through which the suture thread 203 is passed is formed in the section corresponding to the vertex of the triangular shape. The suture thread 203 after passing through the hole 204A of the stopper 204 from the anchor 202 side, is pulled out through the slit 205. The width of the slit 205 becomes larger as the stopper 204 approaches the anchor 202 allowing the suture thread 203 to move. However, in the direction in which the stopper 204 is away from the anchor 202, the slit 205 closes, and the stopper 204 is caught in the suture thread 203 so that it cannot move.

Figure 36:
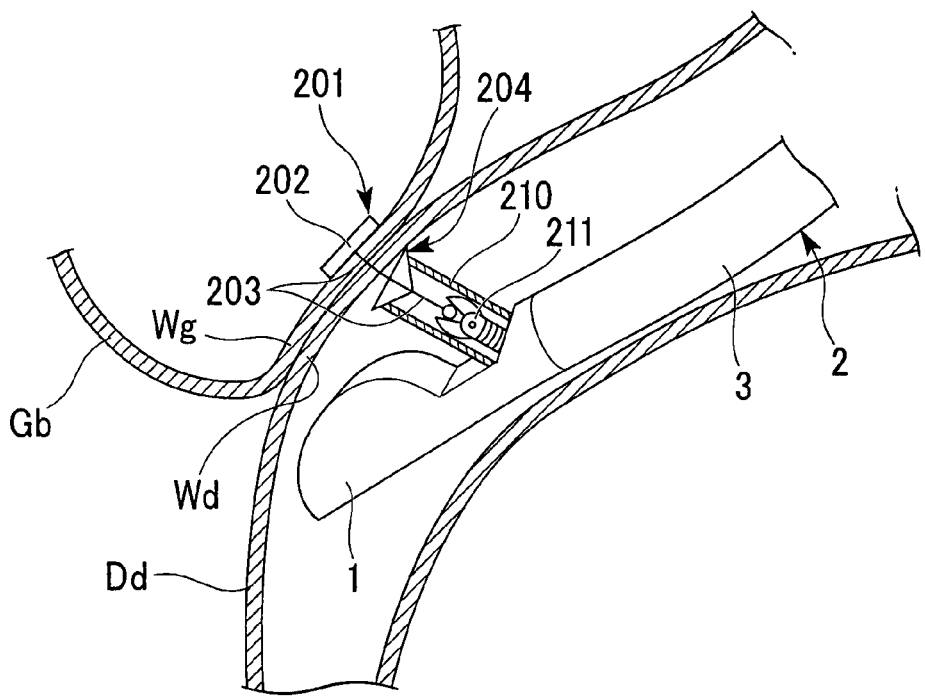
FIG. 36 is a view showing the tissues (gall bladder and duodenum) fastened by anchor and stopper.
Figure 37:
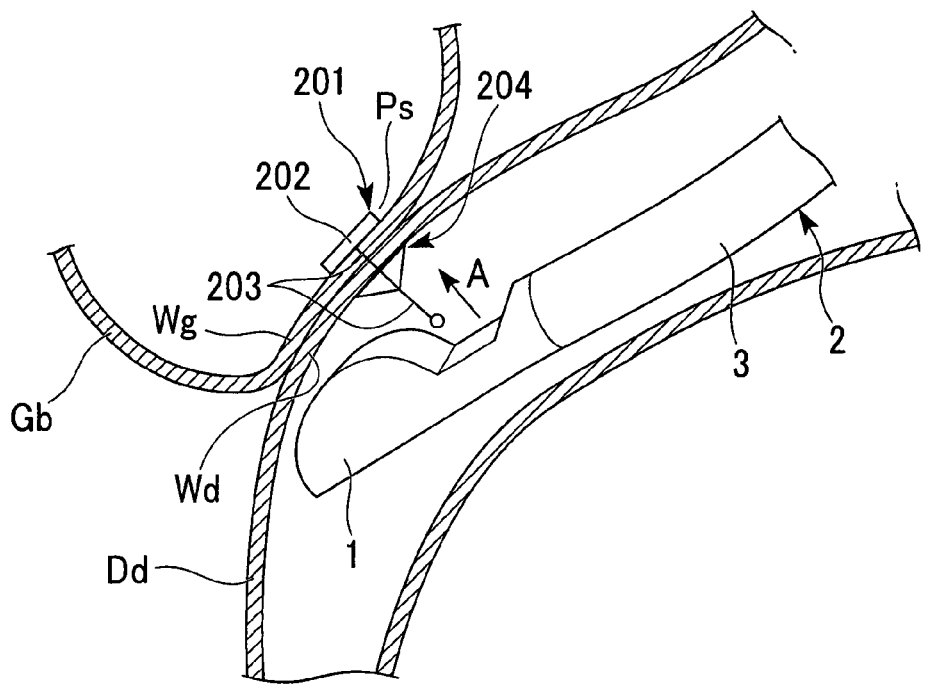
FIG. 37 shows the detained suture tool.
Figure 38:
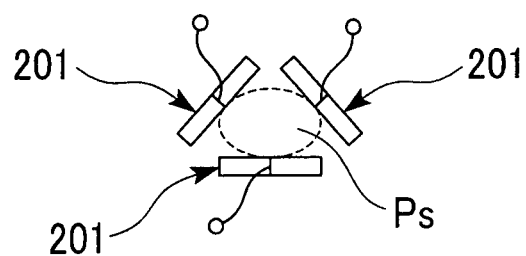
FIG. 38 shows the detained suture tools as seen from A in FIG. 37.

As shown in FIG. 36, the other end of the suture thread 203, pulled out from the stopper 204 with a grasping forceps 211 through the pusher tube 210, is gripped and pulled, and the stopper 204 is pressed in contact with the tissue using the pusher tube 210. The relative motion of the stopper 204 is allowed in this direction. As shown in FIG. 37, the tissues are fastened and fixed by the stopper 204 and the anchor 202, and the close-contact fixed portion Ps is formed. As shown in FIG. 38, the detention tools 201 are detained at a plurality of locations having their center at the location where a puncture is to be formed. That is, a puncture is formed in the range surrounded by the detention tools 210 used as a tool to fix the gall bladder Gb to the duodenum Dd.

Thereafter, using a high-frequency knife or a needle knife, forceps and so on, a puncture is formed in the close-contact fixed portion Ps surrounded by the detention tools 201.

Ninth Embodiment

An example of modification of procedure for forming a close-contact fixed portion between the duodenum wall Wd and the gall bladder wall Wg in step S111 is described here.

Figure 39:
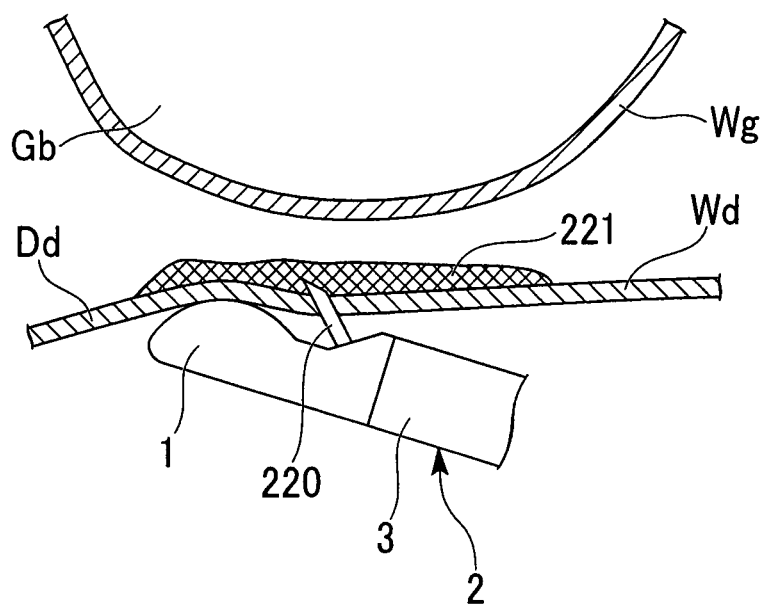
FIG. 39 is an explanatory drawing of the procedure for joining the gall bladder and duodenum by adhesive.
Figure 40:
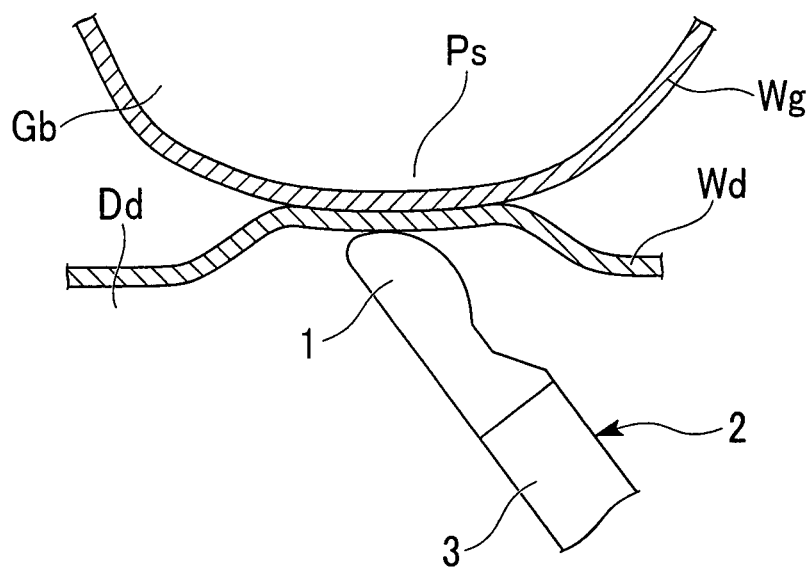
FIG. 40 shows the gall bladder joined by the adhesive.

First, the gall bladder Gb is observed using the ultrasonic probe 1 through the duodenum wall, and after confirming the gall bladder position, the injection needle 220 passing through the endoscope 2 is pierced through the duodenum wall Wd under a guidance of the ultrasonic probe 1, as shown in FIG. 39. At this stage, the gall bladder Gb is not penetrated. Adhesive is delivered through the internal hole in the injection needle 220, and a layer of adhesive 221 is formed on the outside of the duodenum wall Wd. After removing the injection needle 220, the duodenum wall Wd is pressed using the ultrasonic probe 1 while performing ultrasonic observation, and the gall bladder Gb is bonded with the duodenum Dd, as shown in FIG. 40.

Thereafter, using a high-frequency knife or a needle knife, forceps and so on, a puncture is formed in the close-contact fixed portion Ps bonded with adhesive.

In this case also, by bonding the duodenum wall Wd and the gall bladder wall Wg beforehand, bile does not leak and approach to the internal part of gall bladder Gb is possible.

Tenth Embodiment

According to the sixth embodiment, a stent may be detained in the puncture Hc2 in the cases where instead of closing the puncture Hc2, the puncture Hc2 is left open. The procedure to detain the stent is described in this embodiment.

Figure 41:
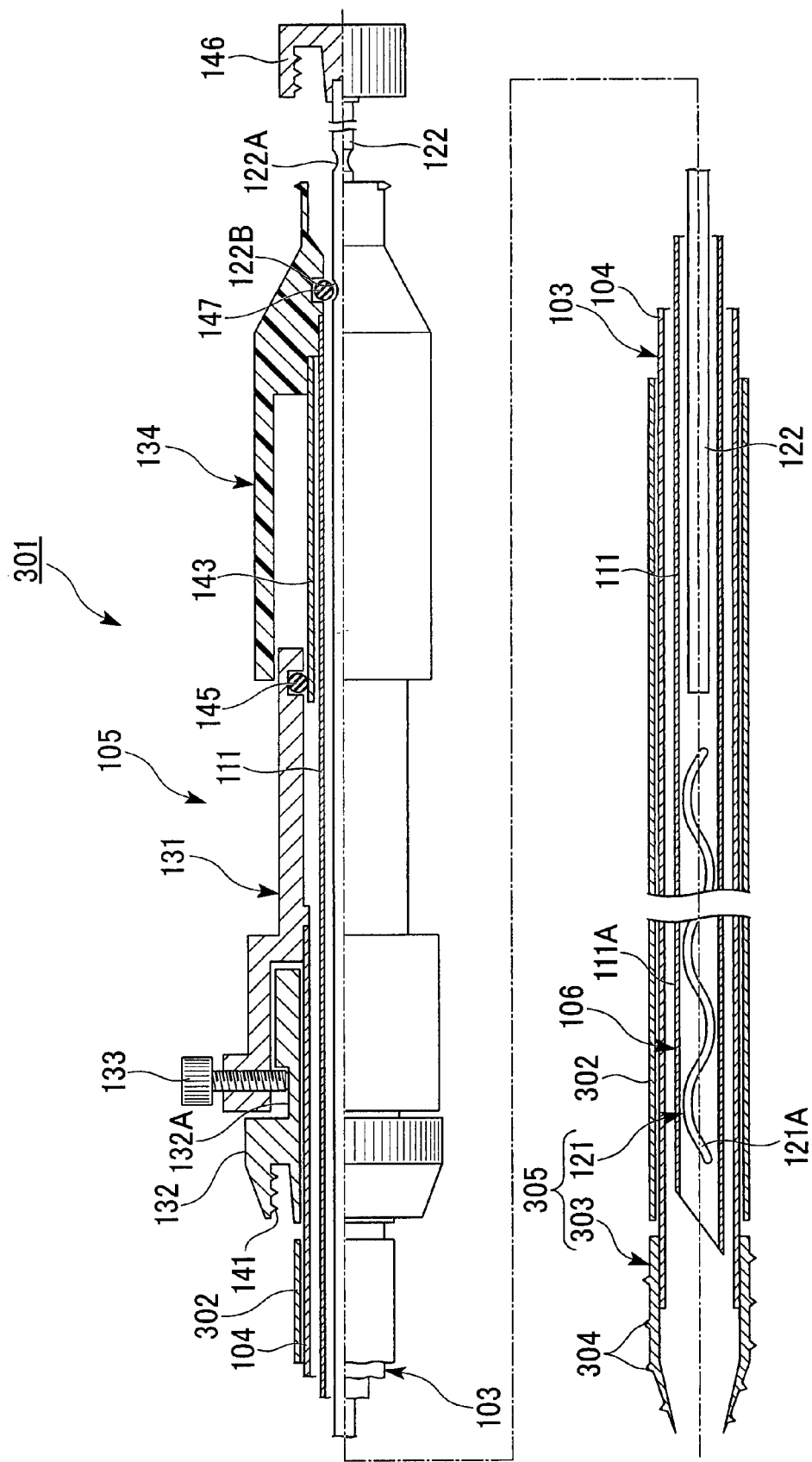
FIG. 41 is a cross sectional view of the applicator when a tissue fastening tool and a stent are used together.

In this procedure, an applicator 301 such as shown in FIG. 41 is used. The applicator 301 has a double-tube sheath construction with the insertion portion 103 provided with a pusher tube 302 on the outside of the sheath 104. A stent 303 is friction fitted at the front end of the sheath 104.

The pusher tube 302 is flexible, and has substantially the same outside diameter as the stent 303. The inside diameter of the pusher tube 302 is slightly larger than the stent 303, and is not engaged the stent 303.

The stent 303 has a cylindrical shape, and its front end has a tapered surface enabling it to be smoothly connected to the outside diameter part of the deployed section 111A. Moreover, a thread 304 formed by ridges in spiral shape is provided on the outer periphery.

Figure 42:
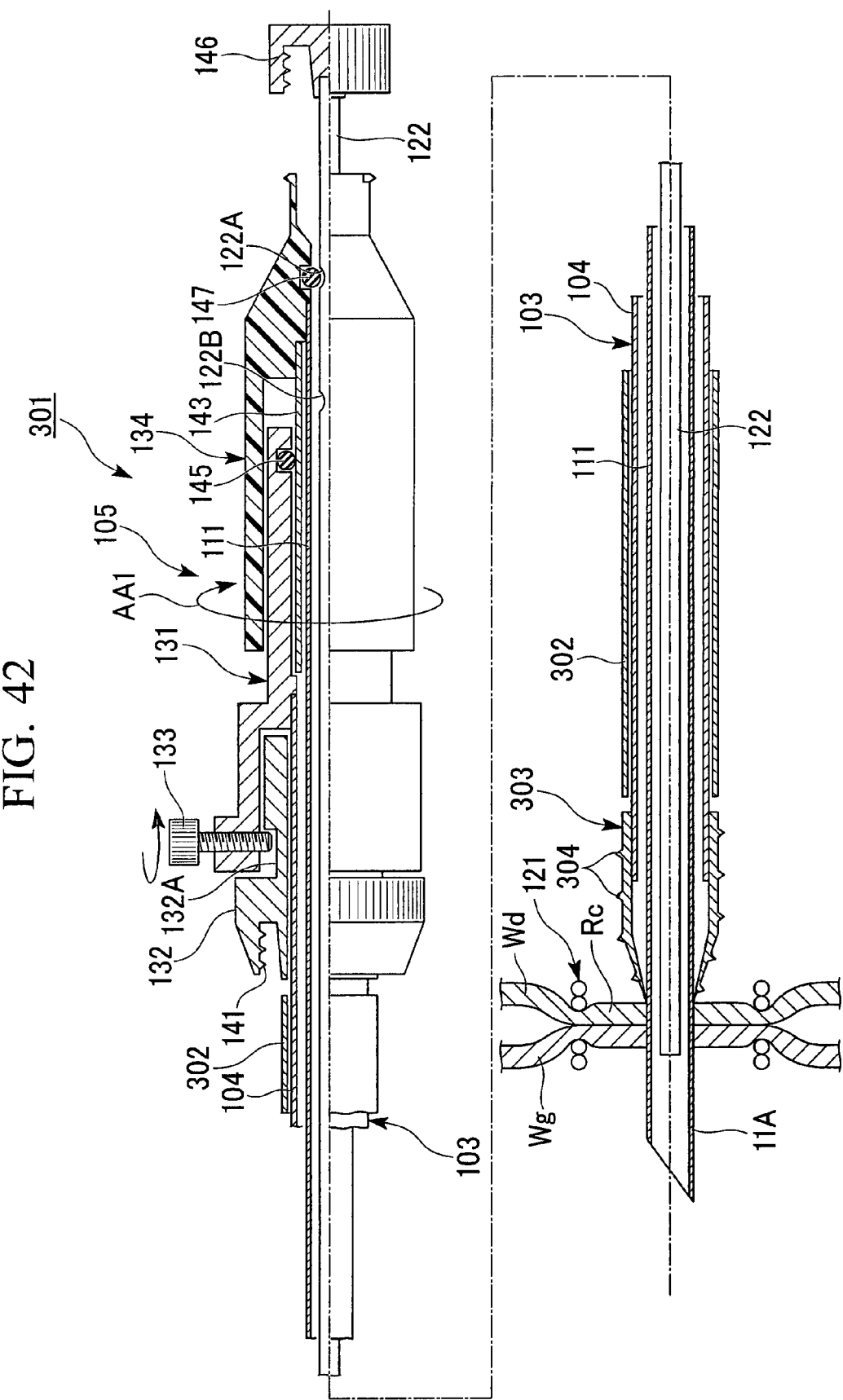
FIG. 42 shows the deployed section piercing the location where a tissue fastening tool is detained, and a stent pressing against the tissue.

As shown in FIG. 42, when the stent 303 is detained, the deployed section 111A is made to pierce the area Rc fastened by the tissue fastening tool 121, and the front end of the stent 303 is deployed to the tissue. At this stage, the stylet 122 is slightly pulled back beforehand, and the incisive front end of the deployed section 111A is used to pierce the area Rc.

Next, the securing screw 133 on the side of the operation part 105 is loosened slightly. The operation part body 131 is rotated around the axial direction with respect to the connector 132 as shown from the view AA1. The sheath 104 fixed to the operation part body 131 rotates, and the stent 303 friction-fitted to it also rotates. Thread 304 is formed on the outer periphery of the stent 303. If the stent 303 is rotated while pressing it against the duodenum wall Wd, the stent 303 is screwed into the duodenum wall Wd and the gall bladder wall Wg, with the through hole formed by the deployed section 111A used as a guide. At this stage, by keeping the stylet 22 pushed in completely, the front end of the stylet 22 protrudes slightly from the front end of the deployed section 11A; therefore, the body cavity tissues are not damaged by the incisive front end of the deployed section 11A.

Since the duodenum wall Wd and the gall bladder wall Wg are fastened by the tissue fastening tool 121, the stent 303 can be detained as if it has been screwed in a single wall. The stent 303 can be adequately screwed into the gall bladder wall Wg by the tissue fastening tool 121, and leakage of bile is prevented.

Figure 43:
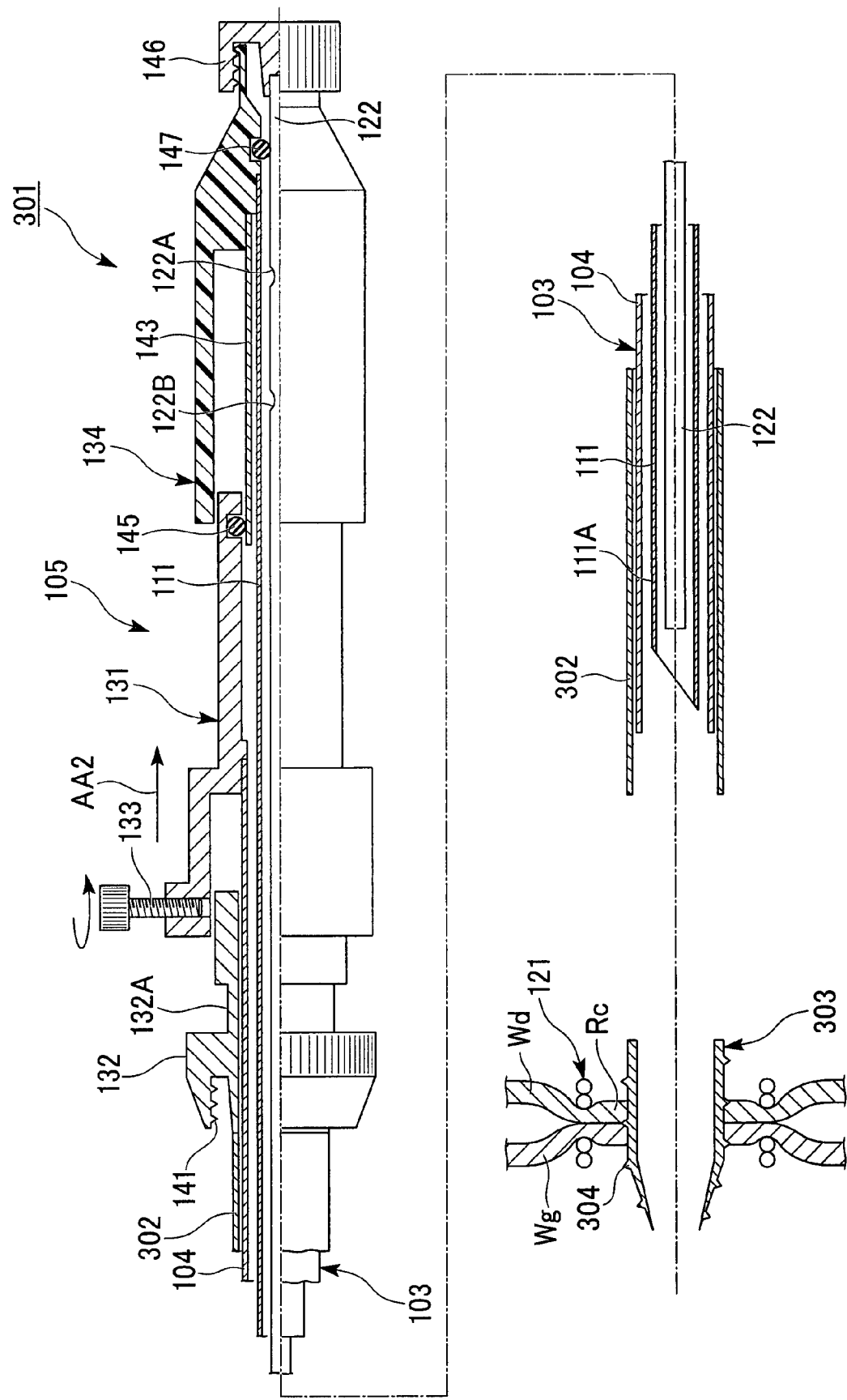
FIG. 43 shows an applicator retracted after the stent has been screwed into the tissue and the stent thereafter released.

When the stent 303 is adequately screwed into the duodenum wall Wd and the gall bladder wall Wg, the stent 303 is separated from the applicator 301. Initially, the deployed section 111A is pulled back and stored in the sheath 104. The securing screw 133 is further loosened such that the operation part body 131 becomes movable in the axial direction after crossing the groove 132A of the connector 132. As shown by view from the arrow AA2, the operation part body 131 is pulled away from the connector 132, and the sheath 104 is retracted. The pusher tube 302 is in contact with the connector 132 and it does not retract. Since the pusher tube 302 does not move, the stent 303 disposed at the front end of the pusher tube 302 also does not move from its position. As a result, the friction fit between the stent 303 and the sheath 104 is loosened, and only the stent 303 is detained, as shown in FIG. 43. The bile will thus be drained through the route ensured by the stent 303 from the gall bladder Gb to the duodenum Dd.

According to the present embodiment, the area of the bile drainage opening can be safely ensured. Also, since the two members, the tissue fastening tool 121 and the stent 303 penetrate the tissue, the misalignment in the direction of rotation of the duodenum Dd and the gall bladder Gb can be reliably prevented.

Figure 44:
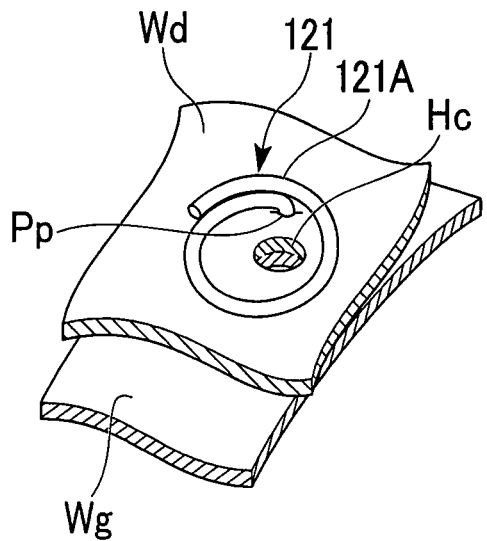
FIG. 44 shows the bile drainage opening formed after detaining the tissue fastening tool.
Figure 45:
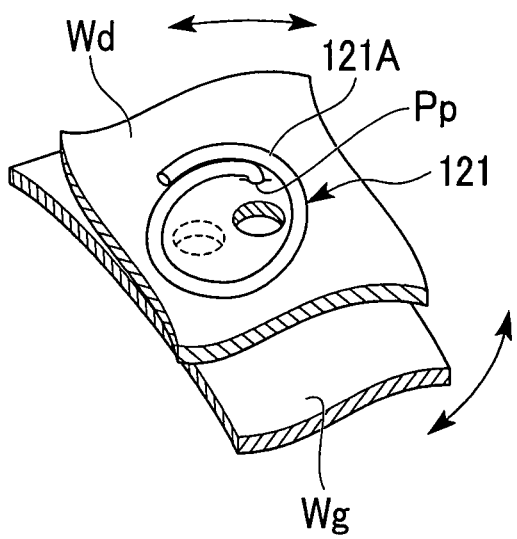
FIG. 45 is an explanatory drawing of the rotation of the duodenum wall and gall bladder, causing misalignment of the drainage opening.

As shown in FIG. 44, the duodenum wall Wd and the gall bladder wall Wg are fastened by the tissue fastening tool 121. When the bile drainage opening is formed by the anastomosis hole Hc penetrating both walls Wd and Wg, the duodenum Dd and the gall bladder Gb may rotate, as shown in FIG. 45, around the center at point Pp through which the element wire 121A penetrates the tissue. In this case, the positions of the bile drainage opening opened in each of the two walls Wd and Wg may become misaligned, and bile drainage may not take place. When the stent 303 is made to penetrate the walls Wd and Wg, the positional relationship between the duodenum Dd and the gall bladder Gb becomes stable, thereby stable bile drainage opening can be ensured.

The shape of the stent is not limited to the stent illustrated above. If the stent connects the gall bladder Gb and the duodenum Dd, and it does not fall off from the tissue, it is anticipated to have similar effects.

Figure 46:
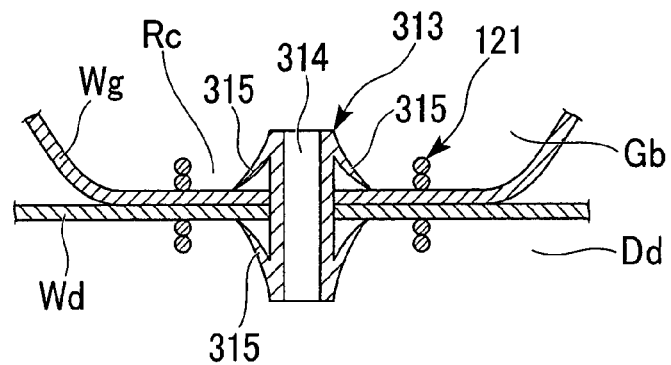
FIG. 46 is a cross sectional view showing an example of modification of stent.
Figure 47:
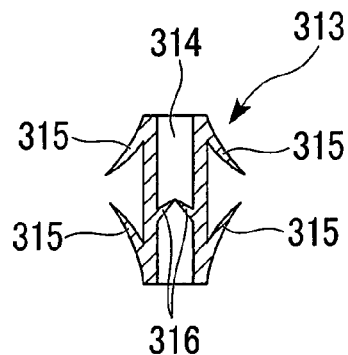
FIG. 47 is a cross sectional view showing a check valve installed in a stent duct.
Figure 48:
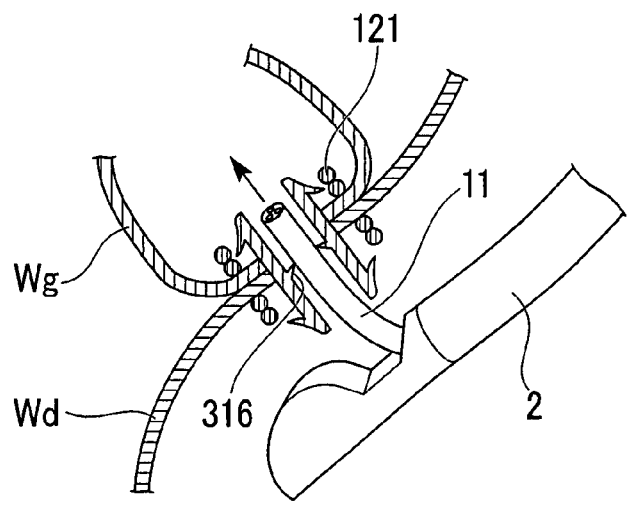
FIG. 48 shows an example of procedure through the stent of FIG. 47.

Moreover, as in the stent 313 shown in FIG. 46, a flap 315 may be provided at the each ends of the tubes 314. The fall-off of stent 313 is prevented. As shown in FIG. 47, by providing a check valve 316 in the tube 314, and using the stent 313, and when a procedure in the gall bladder Gb is performed such as using the endoscope 11 and so on as shown in FIG. 48, particularly when performing a procedure such as cleaning or ablation, the leakage of fluid from the gall bladder Gb to the duodenum Dd side can be prevented. For this reason, the procedure can be performed efficiently. The stent 313 used in this case, has a role similar to that of a trocar in laparoscopic operations.

Eleventh Embodiment

The present embodiment relates to procedure for forming fistulous openings by coalescing and joining the gall bladder and the alimentary tract wall over time when the two have not been coalesced.

Figure 49:
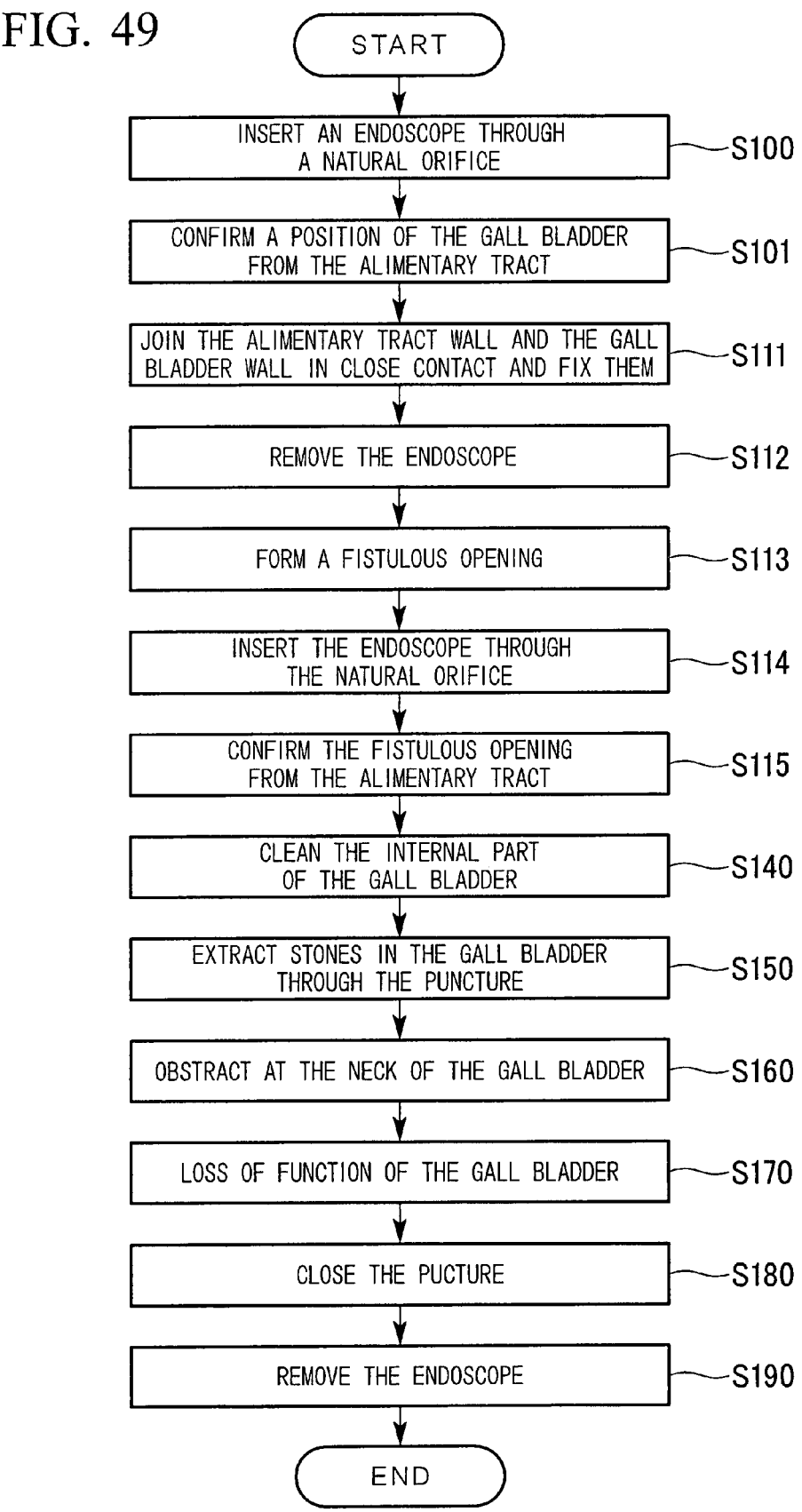
FIG. 49 is a flow chart describing the procedure of the eleventh embodiment.

As shown in FIG. 49, a flexible endoscope 2 is inserted into the duodenum Dd which is the alimentary tract, through a natural orifice (step S100), and the position of the gall bladder Gb is identified (step S101). A close-contact fixed portion is formed between the alimentary tract wall (duodenum wall Wd) and the gall bladder wall Wg (step S111). As described referring to FIG. 26 and FIG. 29, the applicator 101 is inserted in the endoscope 2, and both walls Wd and Wg are brought into close contact and fastened by the tissue fastening tool 121. If necessary, the close-contact fixed portion may be dissected and puncture may be formed. Thereafter, the endoscope 2 is removed, and the patient is recovered in a hospital or at home (step 112).

With the passage of time, the tissue around the area Rc fastened by the tissue fastening tool 121 coalesces and the close-contact fixed portion Ps is formed. The tissue within the area Rc, however, becomes the ischemic condition, so it becomes necrotized and falls off spontaneously. That is, a fistulous opening substantially equal in size to the winding diameter of the coil in the tissue fastening tool 121 containing no foreign substance is formed (step S113).

The shape of the fistulous opening is confirmed, or when the time already preset as the time required for forming the fistulous opening has elapsed, the endoscope 2 is again inserted through a natural orifice (step S114). The formation of the fistulous opening linking the duodenum Dd and the gall bladder Gb in the close-contact fixed portion Ps using the image pickup apparatus of the endoscope 2 is confirmed from the duodenum Dd side (step S115).

Similar to the embodiment mentioned above, the internal parts of the gall bladder Gb is cleaned (step S140), the stones are extracted (step S150), the neck of gall bladder Gn is obstructed (step S160), and the function of the gall bladder Gb is lost (step S170). These procedures are implemented where necessary. For example, when stones have fallen off already from within the gall bladder Gb through the fistulous opening and no more stones remain, or if they are anticipated to fall off spontaneously into the duodenum Dd through the fistulous opening, the extraction is not taken place. The gall bladder Gb may be left to remain as it is, without performing the procedure for losing the function of the epithelial cell of the gall bladder Gb. The cleaning is performed at least once at any timing between the step 115 and the step 170. Instead of the small endoscope 11, the procedure may be made by inserting the endoscope 2 into the gall bladder Gb.

The small endoscope 11 is removed from the fistulous opening, and the fistulous opening is closed (step S180). Finally, the endoscope 2 is removed (step S190). The fistulous opening may be allowed to remain open without closing it.

According to the present embodiment, stones in the gall bladder Gb can be extracted through a natural orifice and forming fistulous openings. For forming fistulous openings, the detention tool 201, as shown in FIG. 38, may be used, and the tissue in the range surrounded by the detention tool 201 may be necrotized so that it falls off.

Figure 50:
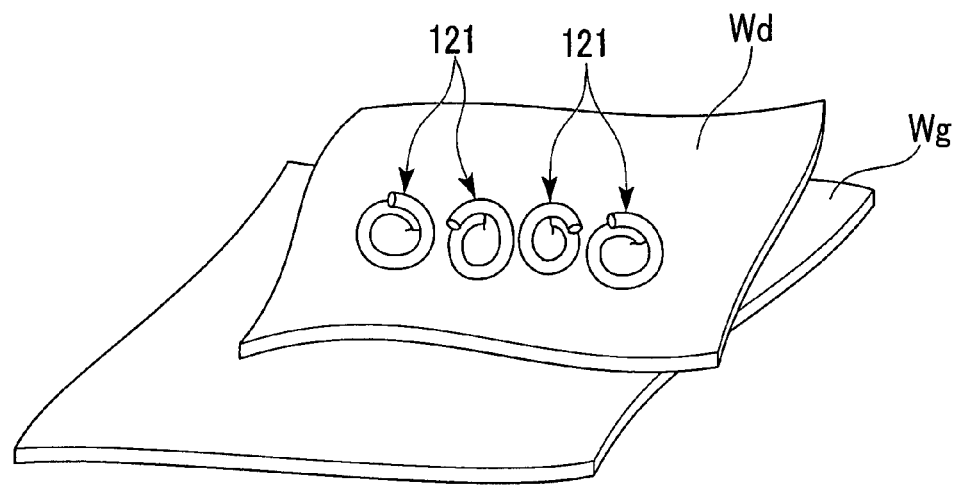
FIG. 50 shows a plurality of tissue fastening tools detained adjacent to each other.

When a large fistulous opening is to be formed, as shown in FIG. 17, balloon 41 may be used and dilated to an adequately large size with respect to the size of stones. As shown in FIG. 50, a plurality of tissue fastening tools 121 may be detained in the tissue in a straight line. The tissue fastening tool 121 used is one in which the fastening force can necrotize the tissue. When each tissue fastening tool 121 falls off together with the tissue that it has necrotized, a continuous elongated hole is formed in the direction in which the tissue fastening tools are arrayed.

Figure 51:
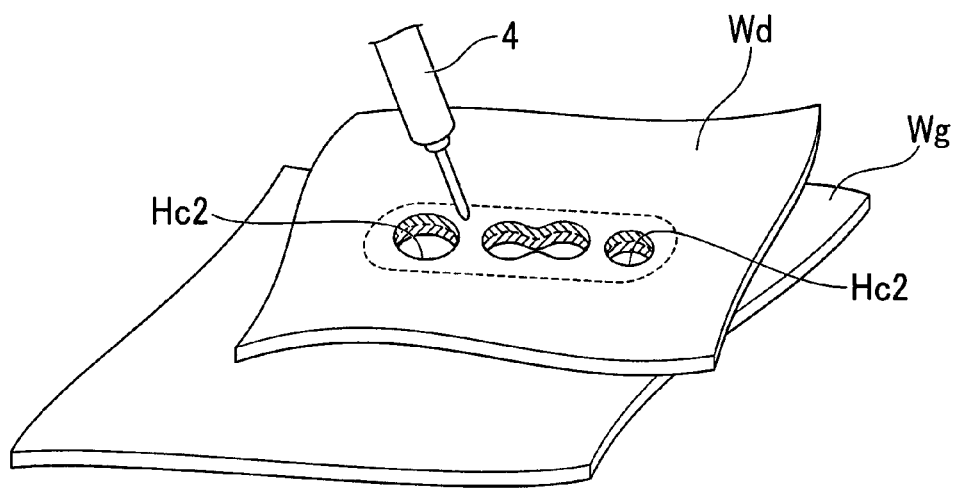
FIG. 51 shows the procedure for joining fistulous openings using a high-frequency knife after the tissue fastening tools has fallen off.
Figure 52:
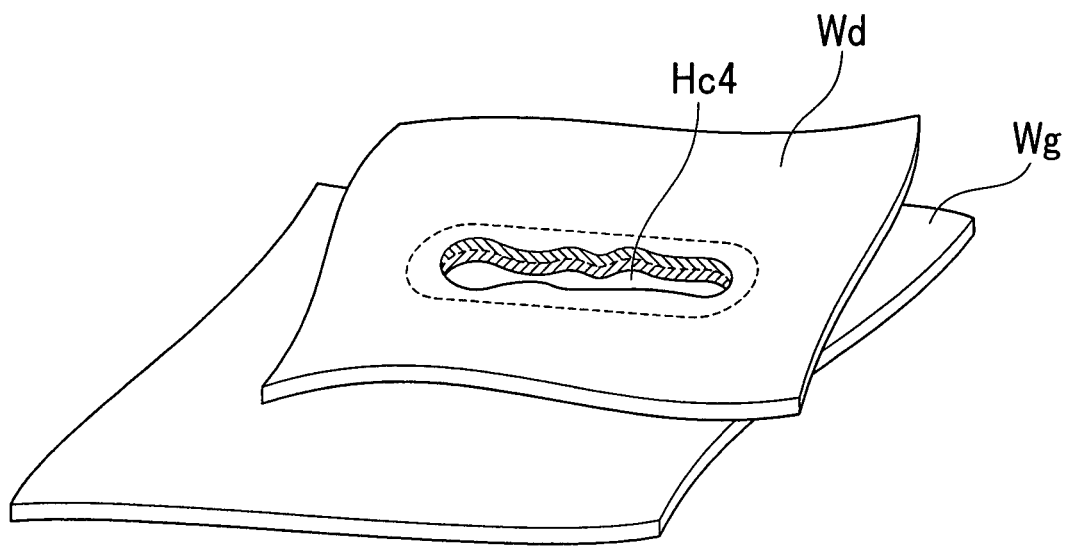
FIG. 52 shows an elongated hole formed by joining fistulous openings.

As shown in FIG. 51, if the punctures Hc2 formed from fistulous openings by the tissue fastening tools 121 are not linked, an incising device such as the high-frequency knife may be used to incise the coalesced portions. The area around the fistulous puncture Hc2 becomes the coalesced range shown by the dotted line. Even if incision is performed within the coalesced range, the bile does not leak from between tissue and tissue. By such incision, a continuous elongated hole Hc4 can be formed, as shown in FIG. 52. The elongated hole Hc4 is not limited to a straight line shaped hole.

The preferred embodiments have been described as above. However, the present invention is not limited to the descriptions above; they are limited only by the scope of claims appended here.

What is claimed is:

1. Application of a procedure through a natural orifice comprising the steps of:
   inserting a flexible endoscope, the endoscope having a channel into which a device is capable of being inserted, through the natural orifice to an alimentary tract;
   verifying positions of the alimentary tract and a gall bladder with a positional relationship identifying device attached to a distal end of the endoscope;
   observing a cross section of the alimentary tract wall and the gall bladder wall under guidance of the positional relationship identifying device;
   verifying the conditions of a coalescence of the alimentary tract and the gall bladder using the positional relationship identifying device;
   incising a coalesced portion between the alimentary tract and the gall bladder under the guidance of the positional relationship identifying device from the alimentary tract side with an incising tool of the device, the incising tool of the device protruding from the channel and forming a puncture into which an image pickup apparatus of a second endoscope and not the positional relationship identifying device is capable of being inserted;
   inserting the an image pickup apparatus of a second endoscope into the gall bladder through the puncture and observing an inside of the gall bladder using the image pickup apparatus of the second endoscope;
   grasping stones in the gall bladder with a grasping tool of the device protruded from the channel; and
   extracting stones in the gall bladder out of the gall bladder via the puncture during observation of the inside of the gall bladder with the image pickup apparatus of the second endoscope.

2. The application of the procedure through the natural orifice according to claim 1, wherein the device for identifying the positional relationship is an ultrasonic probe fitted to the front end of the endo scope.

3. The application of the procedure through the natural orifice according to claim 1, further comprising draining the gall bladder through the puncture.

4. The application of the procedure through the natural orifice according to claim 1, further comprising cleaning the gall bladder through the puncture.

5. The application of the procedure through the natural orifice according to claim 1, further comprising extracting stones in the gall bladder using a device for extraction of stones through an instrument channel of the endoscope.

6. The application of the procedure through the natural orifice according to claim 1, further comprising forming an obstruction at a neck of the gall bladder using a device inserted in the gall bladder.

7. The application of the procedure through the natural orifice according to claim 1, further comprising losing the function of the epithelial cell of the gall bladder.

8. The application of the procedure through the natural orifice according to claim 7, further comprising losing the function of epithelial cell of the gall bladder by thermal ablation.

9. The application of the procedure through the natural orifice according to claim 7, further comprising losing the function of epithelial cell of the gall bladder by chemical ablation.

10. The application of the procedure through the natural orifice according to claim 1, wherein after completing the procedure, the puncture is closed, and thereafter the endoscope is removed.

11. Application of a procedure through a natural orifice comprising the steps of:
inserting a flexible endoscope, having a channel into which a device is capable of being inserted, through the natural orifice to the alimentary tract;
verifying positions of the alimentary tract and a gall bladder using a positional relationship identifying device attached to a distal end of the endoscope;
observing a cross section of the alimentary tract wall and the gall bladder wall under guidance of the positional relationship identifying device;
verifying the conditions of a coalescence using the positional relationship identifying device;
passing a needle of the device, the needle of the device protruding from the channel through the alimentary tract wall;
joining the alimentary tract and the gall bladder in close contact with an adhesive;
forming a puncture in the close-contact portion by using forceps of the device which protrudes from the channel in the alimentary tract;
inserting an image pickup apparatus, not the positional relationship identifying device, with a second endoscope from the alimentary tract into the gall bladder through the puncture and observing an inside of the gall bladder with the image pickup apparatus of the second endoscope;
grasping stones in the gall bladder with a grasping tool of the device protruded from the channel; and
extracting stones in the gall bladder out of the gall bladder via the puncture while checking stones in the gall bladder with the image pickup apparatus of the second endoscope.

12. The application of the procedure through the natural orifice according to claim 11, wherein a fixing tool is used to penetrate the alimentary tract wall and the gall bladder wall when joining the alimentary tract and the gall bladder in close-contact.

13. The application of the procedure through the natural orifice according to claim 11, wherein the alimentary tract wall and the gall bladder wall are bonded to join the alimentary tract and the gall bladder in close contact with each other.

14. The application of the procedure through the natural orifice according to claim 13, further comprising incising the bonded portion and forming the puncture.

15. The application of the procedure through the natural orifice according to claim 11, further comprising incising the tissue within the area surrounded by the fixing tools.

16. The application of the procedure through the natural orifice according to claim 11, further comprising cleaning the gall bladder through the puncture.

17. The application of the procedure through the natural orifice according to claim 11, wherein stones in the gall bladder are extracted using a device for extraction of stones through an instrument channel of the endoscope.

18. The application of the procedure through the natural orifice according to claim 11, further comprising forming an obstruction at a neck of the gall bladder using a device inserted in the gall bladder.

19. The application of the procedure through the natural orifice according to claim 11, further comprising losing the function of the epithelial cell of the gall bladder.

20. The application of the procedure through the natural orifice according to claim 19, further comprising losing the function of epithelial cell of the gall bladder by thermal ablation.

21. The application of the procedure through the natural orifice according to claim 19, further comprising losing the function of epithelial cell of the gall bladder by chemical ablation.

22. The application of the procedure through the natural orifice according to claim 11, wherein after completion of the procedure, the puncture is closed, and thereafter the endoscope is removed.

23. The application of the procedure through the natural orifice according to claim 11, wherein after completing the procedure, the endoscope is removed while leaving the puncture open.

24. The application of the procedure through the natural orifice according to claim 23, wherein after completing the procedure, a stent is passed through the puncture, and thereafter, the endoscope is removed.

25. Application of a procedure through a natural orifice comprising the steps of:
inserting a first flexible endoscope, having a first channel into which a device is capable of being inserted through the natural orifice to the alimentary tract;
verifying positions of the alimentary tract and a gall bladder with a positional relationship identifying device attached to a distal end of the first endoscope;
observing a cross section of the alimentary tract wall and the gall bladder wall under guidance of the positional relationship identifying device;
verifying the conditions of a coalescence using the positional relationship identifying device;
protruding a hollow needle of the device from the first channel, the hollow needle having an opening at a distal end thereof and connected to the opening, the hollow needle having a coil-shaped fixture disposed therein;
passing the hollow needle of the device through both an alimentary tract wall and a gall bladder wall;
forming a fistulous opening between the alimentary tract and the gall bladder while the alimentary tract and the gall bladder are in contact;
after forming the fistulous opening, inserting an image pickup apparatus, not the positional relationship identifying device, of a second endoscope into the gall bladder through the fistulous opening and observing an inside of the gall bladder using the image pickup apparatus of the second endoscope; and
performing the procedure during observation of the inside of the gall bladder using the image pickup apparatus of the second endoscope.

26. The application of the procedure through the natural orifice according to claim 25, further comprising the step of: cleaning the gall bladder through the fistulous opening after forming the fistulous opening.

27. The application of the procedure through the natural orifice according to claim 25, further comprising the step of: extracting stones in the gall bladder with a device for extraction of stones through an instrument channel of the second endoscope after forming the fistulous opening.

28. The application of the procedure through the natural orifice according to claim 25, further comprising the step of: forming an obstruction at the neck of the gall bladder using a device inserted in the gall bladder.

29. The application of the procedure through the natural orifice according to claim 25, further comprising losing the function of the epithelial cell of the gall bladder.

30. The application of the procedure through the natural orifice according to claim 29, further comprising losing the function of epithelial cell of the gall bladder by thermal ablation.

31. The application of the procedure through the natural orifice according to claim 29, wherein the function of epithelial cell of the gall bladder is lost by chemical ablation.

32. The application of the procedure through the natural orifice according to claim 25, wherein after completing the procedure, the puncture is closed, and thereafter the endoscope is removed.

33. The application of the procedure through the natural orifice according to claim 25, wherein after completing the procedure, the second endoscope is removed while leaving the puncture open.

34. The application of the procedure through a natural orifice according to claim 25, further comprising the step of:
- expanding the fistulous opening by using an expanding-fistulous-opening means protruded from a second channel of the second endoscope after forming the fistulous opening and before inserting the second endoscope into the gall bladder.

* * * * *